US006790810B2

(12) United States Patent
Yanagi et al.

(10) Patent No.: US 6,790,810 B2
(45) Date of Patent: Sep. 14, 2004

(54) TETRAZOLINONE DERIVATIVES

(75) Inventors: Akihiko Yanagi, Oyama (JP); Shinichi Narabu, Yuki (JP); Toshio Goto, Tochigi (JP); Seishi Ito, Oyama (JP); Chieko Ueno, Oyama (JP)

(73) Assignee: Nihon Bayer Agrochem K.K., Tyokyo (JP)

(*) Notice: Subject to any disclaimer, the term of this patent is extended or adjusted under 35 U.S.C. 154(b) by 0 days.

(21) Appl. No.: 10/610,301

(22) Filed: Jun. 30, 2003

(65) Prior Publication Data

US 2004/0102635 A1 May 27, 2004

Related U.S. Application Data

(62) Division of application No. 10/049,405, filed as application No. PCT/IB00/01064 on Jul. 28, 2000, now Pat. No. 6,624,121.

(30) Foreign Application Priority Data

Aug. 10, 1999 (JP) ............................................ 11/226845

(51) Int. Cl.$^7$ ...................... A01N 43/713; C07D 403/10
(52) U.S. Cl. ...................................... 504/261; 548/251
(58) Field of Search ........................... 504/261; 548/251

(56) References Cited

U.S. PATENT DOCUMENTS

| | | | | | |
|---|---|---|---|---|---|
| 4,744,815 A | * | 5/1988 | Baba et al. | ...................... | 71/92 |
| 4,885,022 A | * | 12/1989 | Baba et al. | ...................... | 71/86 |
| 4,948,887 A | * | 8/1990 | Baba et al. | .................. | 540/603 |
| 4,954,165 A | * | 9/1990 | Baba et al. | .................... | 71/103 |
| 5,175,299 A | * | 12/1992 | Baba et al. | .................. | 546/248 |
| 5,468,722 A | * | 11/1995 | Shibata et al. | ............... | 504/282 |
| 5,530,135 A | * | 6/1996 | Yanagi et al. | ............... | 548/251 |
| 5,587,484 A | * | 12/1996 | Shibata et al. | ........... | 548/364.4 |
| 5,846,907 A | * | 12/1998 | von Deyn et al. | .......... | 504/221 |
| 6,004,903 A | * | 12/1999 | von Deyn et al. | .......... | 504/239 |
| 6,376,429 B1 | * | 4/2002 | Van Almsick et al. | ...... | 504/271 |

FOREIGN PATENT DOCUMENTS

| | | |
|---|---|---|
| CA | 2075348 | 2/1993 |
| EP | 0 202 929 | 11/1986 |
| EP | 0 203 428 | * 12/1986 |
| EP | 0 282 944 | 9/1988 |
| EP | 0 338 992 | 4/1989 |
| EP | 0 324 221 | 7/1989 |
| EP | 0 869 123 | * 10/1998 |
| JP | 2-222 | 1/1990 |
| JP | 8-134045 | 5/1996 |
| JP | 10-265415 | 10/1998 |
| JP | 10-265441 | 10/1998 |
| JP | 11-12275 | 1/1999 |
| JP | 11-21280 | 1/1999 |
| WO | 96/26192 | * 8/1996 |
| WO | 96/26193 | * 8/1996 |
| WO | 99/03856 | * 1/1999 |
| WO | 99/10327 | 3/1999 |

OTHER PUBLICATIONS

Patent Abstracts of Japan vol. 1999, No. 4, Apr. 30, 1999—&JP 11 012275 A (Nippon Soda Co Ltd), Jan. 19, 1999 abstract.*
Patent Abstracts of Japan vol. 1997, No. 08, Aug. 29, 1997 & JP 09 104602 A (SDS Biotect KK), Apr. 22, 1997 abstract.*
Pesticide Science (month unavailable) 1998, 54, pp. 377–384, The Structure–Activity Relationships of the Triketone Class of HPPD Herbicides, David L. Lee, Christopher G. Knudsen, William J. Michaely, Hsiao–Ling Chin, Nhan H. Nguyen, Charles G. Carter, Thomas H. Cromartie, Byron H. Lake, John M. Shribbs and Torquil Fraser.*
The Journal of Organic Chemistry, vol. 43, No. 10, pp. 2087–2088, May–Aug. 1978 Meldrum's Acid in Organic Synthesis. 2. A General and Versatile Synthesis of B–Keto Esters, Yuji Oikaw, Kiyoshi Sugano, Osamu Yonemitsu.
Weed Science vol. 45, pp. 601–609. (month unavailable) 1997 The discovery and structural requirements of inhibitors of p–hydroxphenylpyruvate dioxygenase, David L. Lee, Michael P. Prisbylla, Thomas H. Cromartie, Derek P. Dagarin, Stott W. Howard, W. Mclean Provan, Martin K. Ellis, Torquil Fraser, Linda C. Mutter.
The Journal of the American Chemical Society vol. 72, May–Aug. 1950, pp. 1888–1891, Phosgene Derivatives. The Preparation of Isocyanates, Carbamyl Chlorides and Cyanuric Acid by R. J. Slocombe, Edgar E. Hardy, J.H. Saunders and R. L. Jenkins.
The Journal of the American Chemical Society, vol. LXXXI Apr.–Jun. 1959, pp. 1523–3172 The Synthesis of 1–Substitued 5(4H) Tetrazolinones by Jerome P. Horwitz, Benjamin E. Fisher and Arthur J. Tomasewski.
The Journal of Organic Chemistry vol. 45, Oct.–Dec. 1980, pp. 5130–5136, Reactions of Trimethylsilyl Azide with Heterocumulenes, Otohiko Tsuge, Satoshi Urano and Koji Oe.

* cited by examiner

Primary Examiner—Patricia L. Morris
(74) Attorney, Agent, or Firm—Richard E. L. Henderson

(57) ABSTRACT

The invention relates to novel tetrazolinone derivatives of general formula (I) wherein $R^1$ represents halogen, $C_{1-4}$ alkyl, $C_{1-4}$ haloalkyl, $C_{1-4}$ alkoxy, $C_{1-4}$ alkylthio, $C_{1-4}$ alkylsulfonyl, $C_{1-4}$ alkylsulfonyloxy, $C_{2-5}$ alkoxycarbonyl, $C_{2-6}$ alkoxyalkyl, $C_{2-6}$ alkylthioalkyl, nitro or cyano, $R^2$ represents a hydrogen atom, $C_{1-6}$ alkyl, $C_{3-6}$ cycloalkyl which may be optionally substituted with halogen, or $C_{1-3}$ alkyl, $C_{1-4}$ haloalkyl or phenyl which may be optionally substituted with halogen, or $C_{1-3}$ aklyl, $C_{1-4}$ haloalkyl or nitro, m represents 0, 1 or 2, n represents 0 or 1, Q represents one of the groups which are mentioned in the description. The invention further relates to their use as herbicides and a process together with the intermediates for their preparation.

5 Claims, No Drawings

TETRAZOLINONE DERIVATIVES

The present patent application is a division of U.S. application Ser. No. 10/049,405, filed Feb. 5, 2002, now U.S. Pat. No. 6,624,121, under 35 U.S.C. 371 as a national stage application of International Application PCT/IB00/01064, filed Jul. 28, 2000, which was published in English as International Patent Publication WO 01/10850 on Feb. 15, 2001, which is entitled to the right of priority of Japanese Application 11/226845, filed Aug. 10, 1999.

BACKGROUND OF THE INVENTION

The present invention relates to novel tetrazolinone derivatives, to processes for their preparation and to their use as herbicides.

It has already been known that certain kinds of tetrazole derivatives show herbicidal activity (Japanese Laid-open Patent Application Nos. 12275/1999 and 21280/1999). Moreover, it has further already been known, that certain kinds of heterocyclic derivatives also show herbicidal activity (U.S. Pat. Nos. 5,834,402 and 5,846,906).

SUMMARY OF THE INVENTION

There have now been found novel tetrazolinone derivatives of the general formula (I)

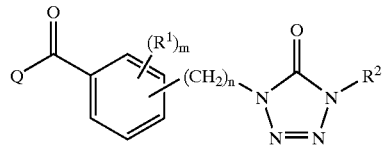
(I)

wherein
- $R^1$ represents halogen, $C_{1-4}$ alkyl, $C_{1-4}$ haloalkyl, $C_{1-4}$ alkoxy, $C_{1-4}$ alkylthio, $C_{1-4}$ alkylsulfonyl, $C_{1-4}$ alkylsulfonyloxy, $C_{2-5}$ alkoxycarbonyl, $C_{2-6}$ alkoxyalkyl, $C_{2-6}$ alkylthioalkyl, nitro or cyano,
- $R^2$ represents a hydrogen atom, $C_{1-6}$ alkyl, $C_{3-6}$ cycloalkyl which may be optionally substituted with halogen or $C_{1-3}$ alkyl, $C_{1-4}$ haloalkyl, or phenyl which may be optionally substituted with halogen, $C_{1-3}$ alkyl, $C_{1-3}$ haloalkyl or nitro,
- m represents 0, 1 or 2; while the two $R^1$ substituents may be identical or different, in case m represents 2,
- n represents 0 or 1, and
- Q represents one of the following groups

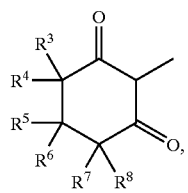
(Q-1)

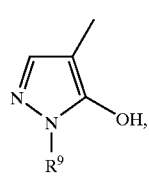
(Q-2)

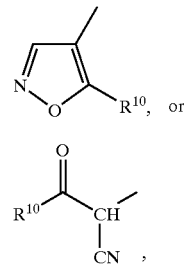
(Q-3)

(Q-4)
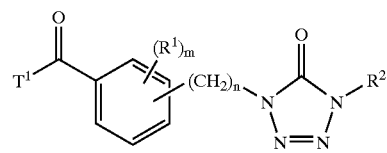

in which
- $R^3$, $R^4$, $R^5$, $R^6$, $R^7$, and $R^8$ each independently represent a hydrogen atom or $C_{1-4}$ alkyl.

or
- $R^3$ and $R^8$ may form an ethylene chain together,
- $R^9$ represents $C_{1-4}$ alkyl,
- $R^{10}$ represents $C_{1-4}$ alkyl or $C_{3-6}$ cycloalkyl which may be optionally substituted with methyl.

The compounds of the general formula (I), according to the invention, can be obtained by a process in which a) compounds of the general formula (IIa)

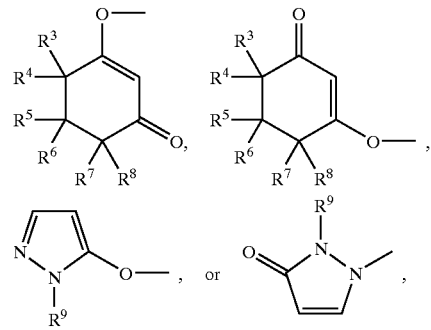
(IIa)

wherein
- $R^1$, $R^2$, m and n have the same definition as aforementioned, and
- $T^1$ represents one of the following groups

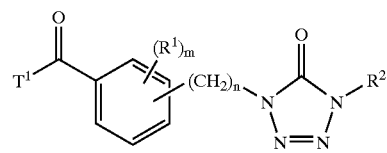

in which
- $R^3$, $R^4$, $R^5$, $R^6$, $R^7$, $R^8$ and $R^9$ have the same definition as mentioned above, are reacted to a rearrangement in the presence of a base and a cyanide, or b) in case that Q represents group (Q-2):

compounds of the general formula (IIb)

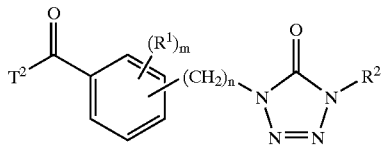

(IIb)

wherein

R$^1$, R$^2$, m and n have the same definitions as mentioned above, and

T$^2$ represents one of the following groups;

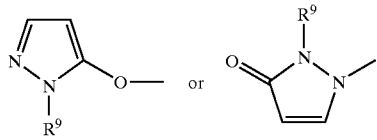

in which

R$^9$ has the same definition as mentioned above, are reacted to a rearrangement in the presence of a base, or c) in case that Q represents group (Q-3):
compounds of the general formula (III)

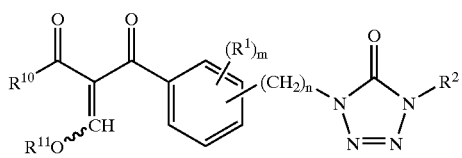

(III)

wherein

R$^1$, R$^2$, R$^{10}$, m and n have the same definitions as mentioned above, and R$^{11}$, represents C$_{1-4}$ alkyl, preferably methyl or ethyl, are reacted with hydroxylamine, or d) in case that Q represents group (Q-4):
compounds of the general formula (Ib)

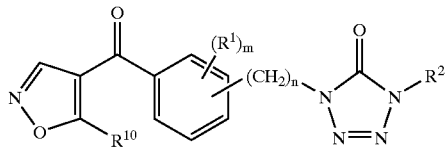

(Ib)

wherein

R$^1$, R$^2$, R$^{10}$, m and n have the same definition as mentioned above, are reacted to a ring-opening in the presence of a base.

DETAILED DESCRIPTION OF THE INVENTION

The tetrazolinone derivatives of the general formula (I) provided by the present invention show a superior herbicidal activity compared with the compounds described in the aforementioned prior art literatures.

In the general formulae:

"Halogen" represents fluoro, chloro, bromo or iodo, and preferably represents fluoro, chloro or bromo.

"Alkyl" may be straight or branched chain and there may be mentioned, for example, C$_{1-6}$ alkyl, specifically methyl, ethyl, n- or iso-propyl, n-, iso-, sec- or tert-butyl, n-, iso-, neo-, or tert-pentyl, n- or iso-hexyl.

As "cycloalkyl" there can be mentioned, for example, cyclopropyl, cyclobutyl, cyclopentyl or cyclohexyl. These cycloalkyls may be optionally substituted with halogen (for example, fluorine, chlorine or bromine), C$_{1-3}$ alkyl (for example, methyl, ethyl, n- or iso-propyl) and in case a plurality of substituents exist, they may be identical or different.

As specific examples of such substituted cycloalkyls there can be mentioned 1-methylcyclopropyl, 1-ethylcyclopropyl, 1-n-propylcyclopropyl, 1-methyl-2-fluorocyclopropyl, 2-methylcyclopropyl, 2-fluorocyclopropyl, 1-methyl-2,2-difluorocyclopropyl, 1-methyl-2,2-dichlorocyclopropyl, 2,2-difluorocyclopropyl, 2-methylcyclopentyl, 1-methylcyclohexyl, 2-methylcyclohexyl, 3-methylcyclohexyl, 4-methylcyclohexyl, 2,3-dimethylcyclohexyl, 2,6-dimethylcyclohexyl, 2,5-dimethylcyclohexyl.

"Haloalkyl" represents straight or branched chain alkyl, of which at least one hydrogen is substituted with halogen, and there may be mentioned, for example, C$_{1-4}$ alkyl substituted with 1 to 6 fluorine atoms and/or chlorine atoms, and more specifically for example difluoromethyl, trifluoromethyl, 2,2,2-trifluoroethyl, dichloromethyl, 2-chloro-1,1,2-trifluoroethyl, 3-fluoropropyl, 3-chloropropyl, 2,2,3,3,3-pentafluoropropyl or 1,2,2,3,3,3-hexafluoropropyl.

"Alkoxy" represents an —O-alkyl group, of which the alkyl part has the above-mentioned meaning. "Alkoxy" and can be, for example, C$_{1-4}$ alkoxy, and more specifically for example methoxy, ethoxy, n- or iso-propoxy, n-, iso-, sec- or tert-butoxy.

"Alkylthio" represents an —S-alkyl group, of which the alkyl part has the above-mentioned meaning. "Alkylthio" can be, for example, C$_{1-4}$ alkylthio, and more specifically for example methylthio, ethylthio, n- or iso-propylthio, n-, iso-, sec- or tert-butylthio.

"Alkylsulfonyl" represents a —SO$_2$-alkyl group, of which the alkyl part has the above-mentioned meaning. "Alkylsulfonyl" can be, for example, C$_{1-4}$ alkylsulfonyl, and more specifically for example methylsulfonyl, ethylsulfonyl, n- or iso-propylsulfonyl, n-, iso-, sec- or tert-butylsulfonyl, "Alkylsulfonyloxy" represents a —O—SO$_2$-alkyl group, of which the alkyl part has the above-mentioned meaning. "Alkylsulfonyloxy" can be, for example, C$_{1-4}$ alkylsulfonyloxy, and more specifically for example methylsulfonyloxy, ethylsulfonyloxy, n- or iso-propylsulfonyloxy, n-, iso-, sec- or tert-butylsulfonyloxy.

"Alkoxycarbonyl" represents a —CO—O-alkyl group, of which the alkyl part has the above-mentioned meaning: "Alkoxycarbonyl" can be, for example, C$_{2-5}$ alkoxycarbonyl, and more specifically for example methoxycarbonyl, ethoxycarbonyl, n- or iso-propoxycarbonyl, n-, iso-, sec- or tert-butoxycarbonyl.

"Alkoxyalkyl" represents alkyl substituted with alkoxy and can be, for example, C$_{2-6}$ alkoxyalkyl, and more specifically for example methoxymethyl, 1-methoxyethyl, 2-methoxyethyl, 2-methoxy-1-methylethyl, methoxypropyl, methoxybutyl, methoxypentyl, ethoxymethyl, n- or iso-propoxymethyl, n-, iso-, sec- or tert-butoxymethyl.

"Alkylthioalkyl" represents alkyl substituted with alkylthio and can be, for example, $C_{2-6}$ alkylthioalkyl, and more specifically for example methylthiomethyl, methylthioethyl, 1-methylthiopropyl, 2-methylthiopropyl, 1-methyl-2-methylthioethyl, methylthiobutyl, methylthiopentyl, ethylthiomethyl, n- or isopropylthiometyl, n-, iso-, sec- or tert-butylthiomethyl.

As a preferred group of compounds of the present invention there can be mentioned the compounds of the aforementioned general formula (I) wherein $R^1$ represents fluoro, chloro, bromo, methyl, ethyl, $C_{1-2}$ haloalkyl, methoxy, ethoxy, methylthio, ethylthio, methylsulfonyl, ethylsulfonyl, methylsulfonyloxy, ethylsulfonyloxy, methoxycarbonyl, ethoxycarbonyl, $C_{2-4}$ alkoxyalkyl, $C_{2-4}$ alkylthioalkyl, nitro or cyano, $R^2$ represents a hydrogen atom, $C_{1-4}$ alkyl $C_{3-5}$ cycloalkyl which may be optionally substituted with fluoro, chloro, bromo or $C_{1-3}$ alkyl $C_{1-3}$ haloalkyl, or phenyl which may be optionally substituted with fluoro, chloro, bromo, methyl, ethyl, difluoromethyl or trifluoromethyl, m represents 0, 1 or 2, while the two $R^1$ substituents may be identical or different, in case m represents 2, n represents 0 or 1, and Q represents one of the following groups (Q-1)

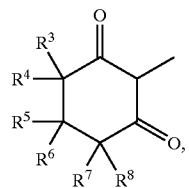

(Q-2)

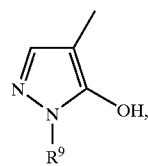

(Q-3)

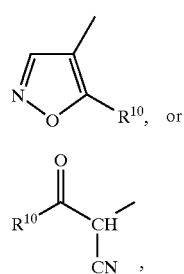

(Q-4)

wherein $R^3$, $R^4$, $R^5$, $R^6$, $R^7$ and $R^8$ each independently represent a hydrogen atom, methyl or ethyl, and $R^3$ and $R^8$ may form an ethylene chain together, $R^9$ represents $C_{1-3}$ alkyl, $R^{10}$ represents tert-butyl or cyclopropyl which may be optionally substituted with methyl.

As a more preferable group of compounds there can be mentioned the compounds of the aforementioned general formula (I) wherein $R^1$ represents chloro, bromo, methyl, trifluoromethyl, methoxy, methylthio, methylsulfonyl, methylsulfonyloxy, methoxycarbonyl, methoxymethyl, methylthiomethyl or nitro, $R^2$ represents a hydrogen atom, methyl, ethyl, n-propyl, isopropyl, tert-butyl, cyclopropyl which may be optionally substituted with fluoro, chloro, methyl, ethyl or n-propyl, difluoromethyl, 2,2,2-trifluoroethyl, 3-fluoropropyl, 2,2,3,3,3-pentafluoropropyl, or phenyl which may be optionally substituted with fluoro, chloro, methyl, difluoromethyl or trifluoromethyl, m represents 0, 1 or 2, while two two $R^1$ substituents may be identical or different, in case m represents 2, n represents 0 or 1, and Q represents one of the following groups

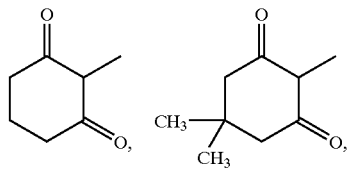

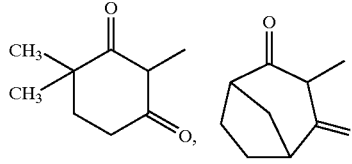

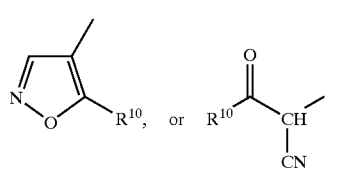

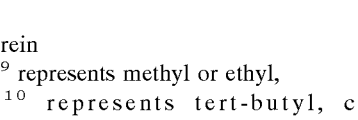

wherein $R^9$ represents methyl or ethyl, $R^{10}$ represents tert-butyl, cyclopropyl or 1-methylcyclopropyl.

The aforementioned preparation process a) is illustrated by the following reaction scheme for the case that for example, 3-oxo-1-cyclohexenly 2,4-dichloro-3-(4,5-dihydro-4-methyl-5-oxo-1H-tetrazol-1-yl)benzoate is used as the starting material.

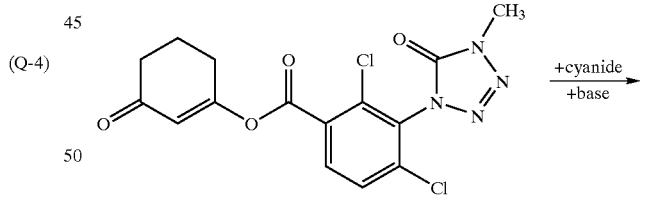

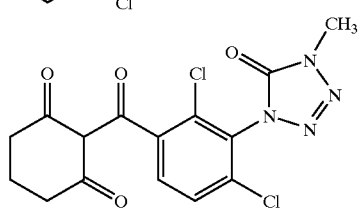

The aforementioned preparation process b) is illustrated by the following reaction scheme for the case that, for example, 5-[2,4-dichloro-3-(4,5-dihydro-4-methyl-5-oxo-1H-tetrazol-1-yl)benzoyloxy]-1-ethylpyrazole or 1-[2,4-dichloro-3-(4,5-dihydro-4-methyl-5-oxo-1H-tetrazol-1-yl)benzoyl]-2-ethyl-2,3-dihydro-1H-3-pyrazolone are used as the starting material.

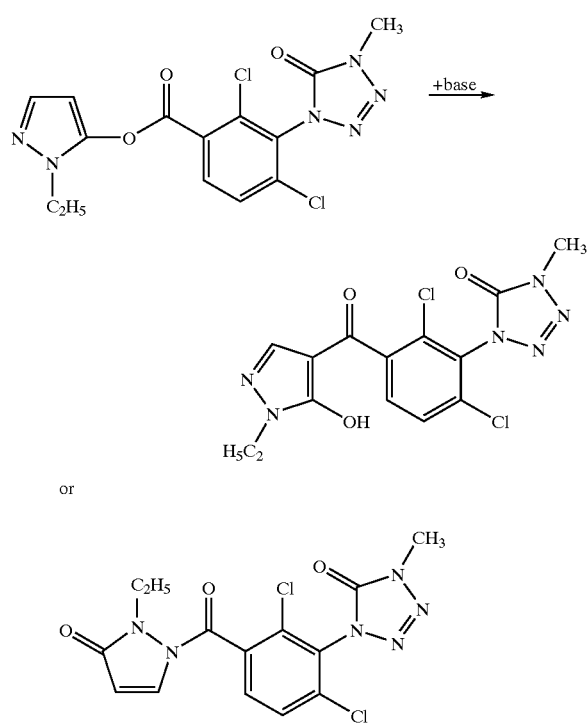

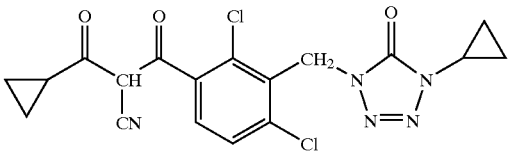

The compounds of the general formula (IIa), the starting material in the above-mentioned preparation process a) are novel compounds which were not described in the literature before the date of application of the present application and can be prepared according to the process described in the literature, for example, Japanese Laid-open Patent Application Nos. 222/1990, 173/1990 and 6425/1990 by reacting compounds of the general formula (IV)

(IV)

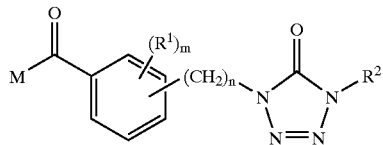

wherein
R$^1$, R$^2$, m and n have the same definition as mentioned above, and
M represents halogen,
with compounds of the general formula (V)

$$Q^1—H \qquad (V)$$

wherein
Q$^1$ represents the following group

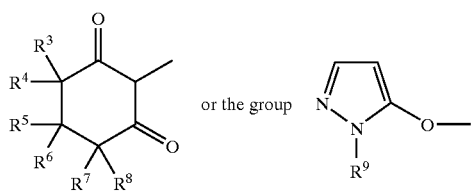

in which
R$^3$, R$^4$, R$^5$, R$^6$, R$^7$, R$^8$ and R$^9$ have the same definition as mentioned above,
in an appropriate diluent, for example, dichloromethane, in the presence of an appropriate condensing agent, for example, triethylamine.

The compounds represented by the above-mentioned general formula (IV) are also novel compounds which were not described in the literature before the date of application of the present application and can be prepared, for example, by reacting compounds of the general formula (VI)

(VI)

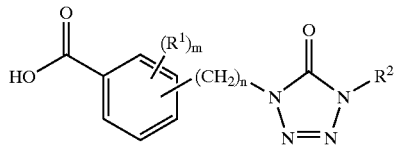

wherein
R$^1$, R$^2$, m and n have the same definition as mentioned above,

The aforementioned preparation process c) is illustrated by the following reaction for the case that, for example, 3-cyclopropyl-1-{3-[(4-cyclopropyl-4,5-dihydro-5-oxo-1H-tetrazol-1-yl)methyl]-2,4-dichlorophenyl}-2-ethoxymethylenepropane-1,3-dione and hydroxylamine is used as the starting material.

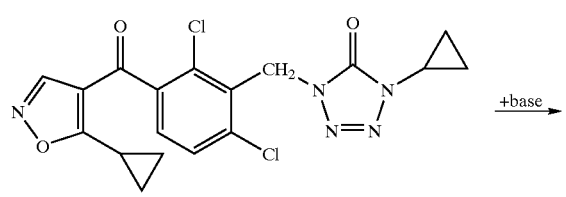

The aforementioned preparation process d) is illustrated by the following reaction scheme for the case that, for example, 5-cyclopropyl-4-{3-[(4-cyclopropyl-4,5-dihydro-5-oxo-1H-tetrazol-1-yl)methyl]-2,4-dichlorobenzoyl}isoxazole is used as the starting material.

with a halogenating agent, for example, phosphorous oxychloride, phosphorous oxybromide, phosphorous trichloride, phosphorous tribromide, phosgene, carbonyl bromide, oxalyl dichloride, thionyl chloride, thionyl bromide.

The compounds of the above-mentioned general formula (V) are commercially available or can be easily prepared according to the processes described in the literature, for example, Japanese Laid-open Patent Application Nos. 6425/1990, 265415/1998, 265441/1998, and 257974/1986.

The compounds of the above-mentioned general formula (VI) are also novel compounds which were not described in the literature before the date of application of the present application and can be prepared, for example, by hydrolyzing compounds of the general formula (VII)

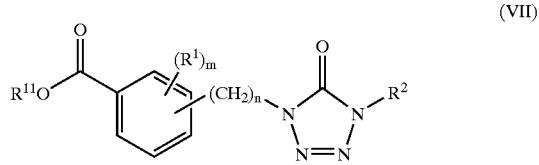

(VII)

wherein
$R^1$, $R^2$, m and n have the same definition as mentioned above, and
$R^{11}$ represents $C_{1-4}$ alkyl, preferably methyl or ethyl,
in an appropriate diluent, for example, aqueous dioxane, in the presence of an appropriate base, for example, sodium hydroxide.

The compounds of the above-mentioned general formula (VII) are also novel compounds and the compounds, in case that n represents 0 in the general formula (VII), can be easily obtained, for example, by reacting compounds of the general formula (VIII)

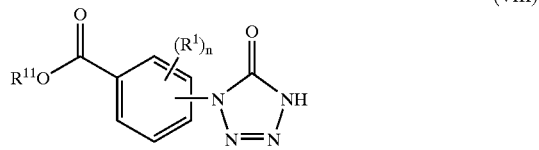

(VIII)

wherein
$R^1$ and m have the same definition as mentioned above, and
$R^{11}$ represents $C_{1-4}$ alkyl, preferably methyl or ethyl,
with compounds of the general formula (IX)

$R^2$–M (IX)

wherein
$R^2$ has the same definition as mentioned above, and
M represents halogen,
in an appropriate diluent, for example, N,N-dimethylformamide, in the presence of an appropriate condensing agent, for example, potassium carbonate.

The compounds of the above-mentioned general formula (VIII) are novel compounds which were not described in the literature before the date of application of the present application and can be easily prepared according to the process described in the literature, for example, Journal of Organic Chemistry, Vol. 45, 5130–5136 (1980), Journal of the American Chemical Society, Vol. 81, 3076–3079 (1959), Journal of the American Chemical Society, Vol. 72, 1888 (1950) by reacting the isocyanic acid esters derived from compounds of the general formula (X)

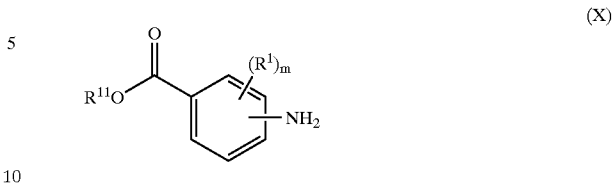

(X)

wherein
$R^1$ and m have the same definition as mentioned above, and
$R^{11}$ represents $C_{1-4}$ alkyl, preferably methyl or ethyl,
with, for example, trimethylsilyl azide or sodium azide.

The compounds of the above-mentioned general formula (IX) are known and commercially available.

The compounds of the above-mentioned general formula (X) are also known and can be easily prepared according to the process described, for example, in Japanese Laid-open Patent Application No. 173/1990.

Further, the compounds of the above-mentioned general formula (VII), in case that n represents 1, can be easily obtained, for example, by reacting compounds of the general formula (XI)

(XI)

wherein
$R^2$ has the same definition as mentioned above,
with compounds of the general formula (XII)

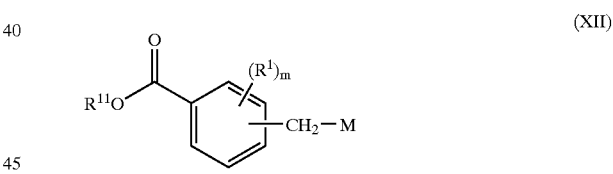

(XII)

wherein
$R^1$ and m have the same definition as mentioned above,
$R^{11}$ represents $C_{1-4}$ alkyl, preferably methyl or ethyl, and
M represents halogen,
in an appropriate diluent, for example, N,N-dimethylformamide, in the presence of an appropriate condensing agent, for example, potassium carbonate.

The compounds of the above-mentioned general formula (XI) are known compounds described, for example, in Japanese Laid-open Patent Application Nos. 97372/1995 and 134045/1996 and can be easily prepared according to the process described in the same references.

The compounds of the above-mentioned general formula (XII), a sub-group of which are novel compounds which were not described in the literature until now, can be easily prepared according to the process described, for example, in Japanese Laid-open Patent Application No. 173/1990.

Furthermore, the compounds of the general formula (IIa), starting material in the above-mentioned preparation process a), can be easily prepared from compounds of the general formula (VI) according to the process described, for example, in WO93/18031.

As typical examples of the compounds of the general formula (IIa), which are used as the starting material in the above-mentioned preparation process a), the following can be mentioned:

3-Oxo-1-cyclohexenyl 2-(4,5-dihydro-4-methyl-5-oxo-1H-tetrazol-1-yl)benzoate, 3-oxo-1-cyclohexenyl 2-[(4,5-dihydro-4-methyl-5-oxo-1H-tetrazol-1-yl)methyl]benzoate, 3-oxo-1-cyclohexenly 2-[(4-cyclohexyl-4,5-dihydro-5-oxo-1H-tetrazol-1-yl)-methyl]-4-fluorobenzoate, 3-oxo-1-cyclohexenyl 4-chloro-2-[(4,5-dihydro-4-methyl-5-oxo-1H-tetrazol-1-yl)methyl]benzoate, 3-oxo-1-cyclohexenyl 4-chloro-2-[(4,5-dihydro-4-ethyl-5-oxo-1H-tetrazol-1-yl)methyl]benzoate, 3-oxo-1-cyclohexenyl 4-chloro-2-[(4-cyclopropyl-4,5-dihydro-5-oxo-1H-tetrazol-1-yl)methyl]benzoate, 3-oxo-1-cyclohexenyl 4-bromo-2-[(4,5-dihydro-4-methyl-5-oxo-1H-tetrazol-1-yl)methyl]benzoate, 3-oxo-1-cyclohexenyl 2-[(4,5-dihydro-4-methyl-5-oxo-1H-tetrazol-1-yl)methyl]-4-trifluoromethylbenzoate, 3-oxo-1-cyclohexenyl 2-(4,5-dihydro-4-ethyl-5-oxo-1H-tetrazol-1-yl)-4-trifluoromethylbenzoate, 3-oxo-1-cyclohexenyl 2-(4,5-dihydro-4-methyl-5-oxo-1H-tetrazol-1-yl)-4-nitrobenzoate, 3-oxo-1-cyclohexenyl 2-(4-difluoromethyl-4,5-dihydro-5-oxo-1H-tetrazol-1-yl)-4-nitrobenzoate, 3-oxo-1-cyclohexenyl 2-[(4,5-dihydro-4-methyl-5-oxo-1H-tetrazol-1-yl)methyl]-4-nitrobenzoate, 3-oxo-1-cyclohexenyl 2-[(4,5-dihydro-4-phenyl-5-oxo-1H-tetrazol-1-yl)methyl]-4-nitrobenzoate, 3-oxo-1-cyclohexenyl 2-(4,5-dihydro-4-methyl-5-oxo-1H-tetrazol-1-yl)-4-methylbenzoate, 3-oxo-1-cyclohexenyl 4-chloro-3-(4,5-dihydro-4-methyl-5-oxo-1H-tetrazol-1-yl)-benzoate, 3-oxo-1-cyclohexenyl 2-chloro-3-(4,5-dihydro-4-methyl-5-oxo-1H-tetrazol-1-yl)-benzoate, 3-oxo-1-cyclohexenyl 4-chloro-3-[(4,5-dihydro-4-methyl-5-oxo-1H-tetrazol-1-yl)methyl]-2-fluorobenzoate, 3-oxo 1-cyclohexenyl 2,4-dichloro-3-(4,5-dihydro-4-methyl-5-oxo-1H-tetrazol-1-yl)-benzoate, 3-oxo-1-cyclohexenyl 2,4-dichloro-3-[4,5-dihydro-4-(3-fluoropropyl)-5-oxo-1H-tetrazol-1-yl]benzoate, 3-oxo-1-cyclohexenyl 2,4-dichloro-3-[4-(n-butyl)-4,5-dihydro-5-oxo-1H-tetrazol-1-yl]benzoate, 3-oxo-1-cyclohexenyl 2,4-dichloro-3-[(4,5-dihydro-4-methyl-5-oxo-1H-tetrazol-1-yl)methyl]benzoate, 3-oxo-1-cyclohexenyl 2,4-dichloro-3-[(4-cyclopropyl-4,5-dihydro-5-oxo-1H-tetrazol-1-yl)methyl]benzoate, 3-oxo-1-cyclohexenyl 2,4-dichloro-3-{[4-(4-bromophenyl)-4,5-dihydro-5-oxo-1H-tetrazol-1-yl]methyl}benzoate, 3-oxo-1-cyclohexenyl 2-chloro-3-(4,5-dihydro-4-methyl-5-oxo-1H-tetrazol-1-yl)-4-methylsulfonylbenzoate, 3-oxo-1-cyclohexenyl 2-chloro-3-[(4,5-dihydro-4-methyl-5-oxo-1H-tetrazol-1-yl)methyl]-4-methylsulfonylbenzoate, 3-oxo-1-cyclohexenyl 2-chloro-3-[(4-cyclopropyl-4,5-dihydro-5-oxo-1H-tetrazol-1-yl)methyl]-4-methylsulfonylbenzoate, 3-oxo-1-cyclohexenyl 2-chloro-3-{[4,5-dihydro-4-(n-pentyl)-5-oxo-1H-tetrazol-1-yl]methyl}-4-methylsulfonylbenzoate, 3-oxo-1-cyclohexenyl 2-chloro-3-{[4-(3-difluoromethylphenyl)-4,5-dihydro-5-oxo-1H-tetrazol-1-yl]methyl}-4-methylsulfonylbenzoate, 3-oxo-1-cyclohexenyl 4-chloro-3-(4,5-dihydro-4-methyl-5-oxo-1H-tetrazol-1-yl)-2-methylthiobenzoate, 3-oxo-1-cyclohexenyl 4-chloro-3-[(4,5-dihydro-4-methyl-5-oxo-1H-tetrazol-1-yl)methyl]-2-methylthiobenzoate, 3-oxo-1-cyclohexenyl 2,4-di(methylthio)-3-[(4,5-dihydro-4-methyl-5-oxo-1H-tetrazol-1-yl)methyl]benzoate, 3-oxo-1-cyclohexenyl 4-chloro-3-(4,5-dihydro-4-methyl-5-oxo-1H-tetrazol-1-yl)-2-methylsulfonylbenzoate, 3-oxo-1-cyclohexenyl 4-chloro-3-[(4,5-dihydro-4-methyl-5-oxo-1H-tetrazol-1-yl)methyl]-2-methylsulfonylbenzoate, 3-oxo-1-cyclohexenyl 4-(4,5-dihydro-4-methyl-5-oxo-1H-tetrazol-1-yl)-3-methoxybenzoate, 3-oxo-1-cyclohexenyl 2-chloro-4-(4,5-dihydro-4-methyl-5-oxo-1H-tetrazol-1-yl)benzoate, 3-oxo-1-cyclohexenyl 2-chloro-4-(4,5-dihydro-4-isopropyl-5-oxo-1H-tetrazol-1-yl)benzoate, 3-oxo-1-cyclohexenyl 2-chloro-4-[(4,5-dihydro-4-methyl-5-oxo-1H-tetrazol-1-yl)methyl]benzoate, 3-oxo-1-cyclohexenyl 2-bromo-4-(4,5-dihydro-4-methyl-5-oxo-1H-tetrazol-1-yl)benzoate, 3-oxo-1-cyclohexenyl 4-[(4,5-dihydro-4-methyl-5-oxo-1H-tetrazol-1-yl)methyl]-2-methoxybenzoate, 3-oxo-1-cyclohexenyl 4-{[4-(2-chlorophenyl)-4,5-dihydro-5-oxo-1H-tetrazol-1-yl]methyl}-2-methoxybenzoate, 3-oxo-1-cyclohexenyl 4-[(4-cyclopropyl-4,5-dihydro-5-oxo-1H-tetrazol-1-yl)methyl]-2-methylsulfonyloxybenzoate, 3-oxo-1-cyclohexenyl 4-(4,5-dihydro-4-methyl-5-oxo-1H-tetrazol-1-yl)-2-nitrobenzoate, 3-oxo-1-cyclohexenyl 4-[(4,5-dihydro-4-methyl-5-oxo-1H-tetrazol-1-yl)methyl]-2-nitrobenzoate, 5,5-dimethyl-3-oxo-1-cyclohexenyl 2-[(4,5-dihydro-4-methyl-5-oxo-1H-tetrazol-1-yl)methyl]-4-trifluoromethylbenzoate, 5,5-dimethyl-3-oxo-1-cyclohexenyl 2,4-dichloro-3-(4,5-dihydro-4-methyl-5-oxo-1H-tetrazol)-1-yl)benzoate, 4,4-dimethyl-3-oxo-1-cyclohexenyl 4-bromo-2-[(4,5-dihydro-4-methyl-5-oxo-1H-tetrazol-1-yl)methyl]benzoate, 4,4-dimethyl-3-oxo-1-cyclohexenly 2,4-dichloro-3-[(4,5-dihydro-4-methyl-5-oxo-1H-tetrazol-1-yl)methyl]benzoate, 4-{4-choloro-2-[(4,5-dihydro-4-methyl-5-oxo-1H-tetrazol-1-yl)methyl]benzoyloxy}-bicyclo[3.2.1]-3-octen-2-one, 4-{2,4-dichloro-3-[(4-cyclopropyl-4,5-dihydro-5-oxo-1H-tetrazol-1-yl)methyl]-benzoyloxybicyclo[3.2.1]-3-octen-2-one, 5-{2-[(4,5-dihydro-4-methyl-5-oxo-1H-tetrazol-1-yl)methyl]-4-fluorobenzoyloxy}-1-methylpyrazole, 5-{4-bromo-2-[(4,5-dihydro-4-methyl-5-oxo-1H-tetrazol-1-yl)methyl]benzoyloxy}-1-ethylpyrazole, 5-{4-bromo-2-[(4,5-dihydro-4-methyl-5-oxo-1H-tetrazol-1-yl)methyl]benzoyloxy}-1-methylpyrazole, 5-{2-[(4,5-dihydro-4-(n-propyl)-5-oxo-1H-tetrazol-1-yl)methyl]-4-trifluoromethylbenzoyloxy}-1-methylpyrazole, 5-[2-(4,5-dihydro-4-methyl-5-oxo-1H-tetrazol-1-yl)-4-methylbenzoyloxy]-1-ethylpyrazole, 5-[2-(4,5-dihydro-4-methyl-5-oxo-1H-tetrazol-1-yl)-4-trifluoromethylbenzoyloxy]-1-ethylpyrazole, 5-[2,4-dichloro-3-(4,5-dihydro-4-methyl-5-oxo-1H-tetrazol-1-yl)benzoyloxy]-1-ethylpyrazole, 5-{2,4-dichloro-3-{[4-(tert-butyl)-4,5-dihydro-5-oxo-1H-tetrazol-1-yl]methyl}benzoyloxy}-1-ethylpyrazole, 5-[2-chloro-3-(4,5-dihydro-4-methyl-5-oxo-1H-tetrazol-1-yl)-4-trifluoromethylsulfonylbenzoyloxy]-1-ethylpyrazole, 5-{2-chloro-3-[(4,5-dihydro-4-methyl-5-oxo-1H-tetrazol-1-yl)methyl]-4-methylsulfonylbenzoyloxy}-1-ethylpyrazole, 5-[4-chloro-3-(4,5-dihydro-4-methyl-5-oxo-1H-tetrazol-1-yl)-2-methylthiobenzoyloxy]-1-ethylpyrazole, 5-{4-chloro-3-[(4,5-dihydro-4-methyl-5-oxo-1H-tetrazol-1-yl)methyl]-2-methylthiobenzoyloxy}-1-methylpyrazole, 5-{2,4-di(methylthio)-3-[(4,5-dihydro-4-methyl-5-oxo-1H-tetrazol-1-yl)methyl]-benzoyloxy}-1-ethylpyrazole, 5-[4-chloro-3-(4,5-dihydro-4-methyl-5-oxo-1H-tetrazol-1-yl)-2-methylsulfonylbenzoyloxy]-1-ethylpyrazole, 5-{4-chloro-3-[(4,5-dihydro-4-methyl-5-oxo-1H-tetrazol-1-yl)methyl]-2-methylsulfonylbenzoyloxy}-1-ethylpyrazole, 5-[2-chloro-4-(4,5-dihydro-4-methyl-5-oxo-1H-tetrazol-1-yl)benzoyloxy]-1-ethylpyrazole, 5-[2-chloro-4-(4-difluormethyl-4,5-dihydro-5-oxo-1H-tetrazol-1-yl)benzoyloxy]-1-methylpyrazole, 5-{2-chloro-4-[(4-cyclopropyl-4,5-dihydro-5-oxo-1H-tetrazol-1-yl)methyl]benzoyloxy}-1-ethylpyrazole, 5-[2-bromo-4-(4,5-dihydro-4-ethyl-5-oxo-1H-tetrazol-1-yl)benzoyloxy]-1-methylpyrazole, 5-{4-[(4-cyclopropyl-4,5-dihydro-5-oxo-1H-tetrazol-1-yl)methyl]-2-methoxybenzoyloxy}-1-ethylpyrazole, 5-{4-[(4,5-dihydro-4-methyl-5-oxo-1H-tetrazol-1-yl)methyl]-2-methylsulfonyloxybenzoyloxy}-1-ethylpyrazole, 5-[4-(4,5-dihydro-4-methyl-5-oxo-1H-tetrazol-1-yl)-2-nitrobenzoyloxy]-1-methylpyrazole, 5-{4-[(4-cyclopropyl-4,5-dihydro-5-oxo-1H-tetrazol-1-yl)methyl]-2-nitrobenzoyloxy}-1-ethylpyrazole.

The compounds of the general formula (IIb), the starting material in the above-mentioned preparation process b), are a sub-group of the compounds of the aforementioned general formula (IIa).

The compounds of the general formula (III), the starting material in the above-mentioned preparation process c), are novel compounds, which were not described in the literature before the date of application of the present application, and can be prepared according to the process described, for example, in Japanese Laid-open Patent Application No. 202008/1993 by reacting compounds of the general formula (XIII)

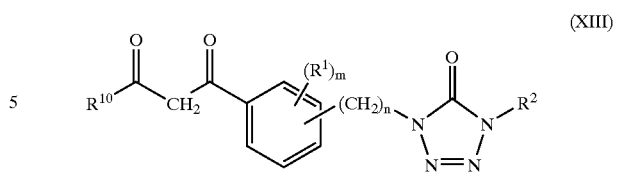

wherein
$R^1$, $R^2$, $R^{10}$, m and n have the same definition as mentioned above,
with compounds of the general formula (XIV)

wherein
$R^{11}$ has the same definition as aforementioned,
in an appropriate diluent, for example, acetic anhydride.

The compounds of the above-mentioned general formula (XIII) are novel compounds, which were not described in the literature before the date of application of the present application, and can be prepared according to the process described, for example, in Japanese Laid-open Patent Application No. 202008/1993 by reacting compounds of the general formula (XV)

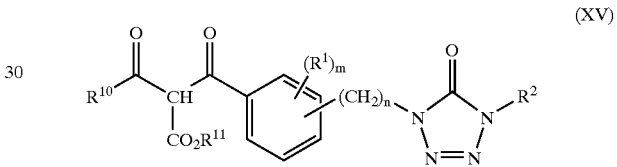

wherein
$R^1$, $R^2$, $R^{10}$, m, n and $R^{11}$ have the same definition as aforementioned,
under an appropriate acidic condition in an appropriate diluent, for example, toluene in the presence of, for example, p-toluenesulfonic acid monohydrate.

The compounds of the above-mentioned general formula (XV) are novel compounds, which were not described in the literature before the date of application of the present application, and can be prepared according to the process described, for example, in Japanese Laid-open Patent Application No. 202008/1993 by reacting compounds of the above-mentioned general formula (IV) with, for example, a complex obtained by treating compounds of the general formula (XVI)

wherein
$R^{10}$ has the same definition as aforementioned,
$R^{12}$ represents $C_{1-4}$ alkyl,
with magnesium and carbon tetrachloride.

The compounds of the above-mentioned general formula (XVI) are commercially available or can be prepared according to the process described, for example, in Journal of Organic Chemistry, Vol. 43, 2087 (1978).

The compounds of the above-mentioned general formula (XVI) are already known.

As typical examples of the compounds of the general formula (III), which are used as the starting material in the above-mentioned preparation process c), the following can be mentioned:

3-Cyclopropyl-1-{2-[(4,5-dihydro-4-ethyl-5-oxo-1H-tetrazol-1-yl)methyl]-4-fluoro-phenyl}-2-ethoxymethylenepropan-1,3-dione, 3-cyclopropyl-1-{4-chloro-2-[(4,5-dihydro-4-ethyl-5-oxo-1H-tetrazol-1-yl)methyl]-phenyl}-2-ethoxymethylenepropan-1,3-dione, 3-cyclopropyl-1-{2-[(4-cyclopropyl-4,5-dihydro-5-oxo-1H-tetrazol-1-yl)methyl]-4-trifluoromethylphenyl}-2-ethoxymethylenepropan-1,3-dione, 3-cyclopropyl-1-[2-(4,5-dihydro-4-methyl-5-oxo-1H-tetrazol-1-yl)-4-trifluoromethylphenyl]-2-ethoxymethylenepropan-1,3-dione, 3-cyclopropyl-1-{4-chloro-3-[(4-cyclopropyl-4,5-dihydro-5-oxo-1H-tetrazol-1-yl)-methyl]-2-fluorophenyl}-2-ethoxymethylenepropan-1,3-dione, 3-cyclopropyl-1-[2,4-dichloro-3-(4,5-dihydro 4-methyl-5-oxo-1H-tetrazol-1-yl)phenyl]-2-ethoxymethylene-propan-1,3-dione, 3-cyclopropyl-1-{3-[(4-cyclopropyl-4,5-dihydro-5-oxo-1H-tetrazol-1-yl)methyl]-2,4-dichlorophenyl}-2-ethoxymethylenepropan-1,3-dione, 3-cyclopropyl-1-{2-chloro-3-[(4,5-dihydro-4-methyl-5-oxo-1H-tetrazol-1-yl)methyl]-4-methylsulfonyl-phenyl}-2-ethoxymethylenepropan-1,3-dione, 3-cyclopropyl-1-[4-chloro-3-(4,5-dihydro-4-methyl-5-oxo-1H-tetrazol-1-yl)-2-methylthiophenyl]-2-ethoxymethylenepropan-1,3-dione, 3-cyclopropyl-1-{4-chloro-3-[(4,5-dihydro-4-methyl-5-oxo-1H-tetrazol-1-yl)methyl]-2-methylsulfonyl-phenyl}-2-ethoxymethylenepropan-1,3-dione, 3-cyclopropyl-1-[2-chloro-4-(4,5-dihydro-4-methyl-5-oxo-1H-tetrazol-1-yl)phenyl]-2-ethoxymethylene-propan-1,3-dione, 3-(tert-butyl)-1-{2-chloro-3-[(4,5-dihydro-4-methyl-5-oxo-1H-tetrazol-1-yl)methyl]-4-methylsulfonyl-phenyl}-2-ethoxymethylenepropan-1,3-dione.

The compounds of the general formula (Ib), the starting material in the above-mentioned preparation process d), are a sub-group of the compounds of the general formula (I) of the present invention and can be easily prepared according to the above-mentioned preparation process c).

As typical examples of the compounds of the general formula (Ib), which are used as the starting material in the above-mentioned preparation process (d), there can be mentioned the following which are included in the general formula (I):

4-{4-Chloro-2-[(4,5-dihydro-4-methyl-5-oxo-1H-tetrazol-1-yl)methyl]benzoyl}-5-cyclopropylisoxazole, 5-cyclopropyl-4 [2-(4,5-dihydro-4-methyl-5-oxo-1H-tetrazol-1-yl)-4-nitrobenzoyl]-isoxazole, 4-{2-[(4-cyclohexyl-4,5-dihydro-5-oxo-1H-tetrazol-1-yl) methyl]-4-nitrobenzoyl}-5-cyclopropylisoxazole, 4-[2,4-dichloro-3-(4,5-dihydro-4-methyl-5-oxo-1H-tetrazol-1-yl)benzoyl]-5-cyclopropylisoxazole, 4-{2,4-dichloro-3-[(4,5-dihydro-4-methyl-5-oxo-1H-tetrazol-1-yl)methyl]benzoyl}-5-cyclopropylisoxazole, 4-{2-chloro-3-[(4,5-dihydro-4-methyl-5-oxo-1H-tetrazol-1-yl)methyl]-4-methyl-sulfonylbenzoyl}-5-cyclopropylisoxazole, 4-{4-chloro-3-[(4,5-dihydro-4-methyl-5-oxo-1H-tetrazol-1-yl)methyl]-2-methylthio-benzoyl}-5-cyclopropylisoxazole, 4-[2-chloro-4-(4,5-dihydro-4-methyl-5-oxo-1H-tetrazol-1-yl)benzoyl]-5-cyclopropyl-isoxazole.

The general formulae (IIa), (IIb), (III), (IV), (VI), (VII), (VIII), (XIII) and (XV) of the novel starting materials and intermediates in the preparation processes of the compounds of the above-mentioned general formula (I) of the present invention can be represented collectively by the following general formula (XVII)

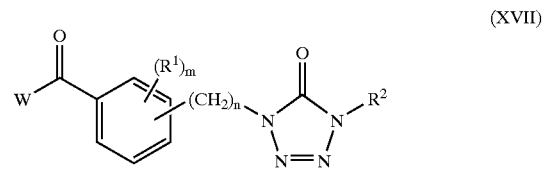

(XVII)

wherein

W represents $T^1$, M, hydroxy, or one of the following groups $OR^{11}$,

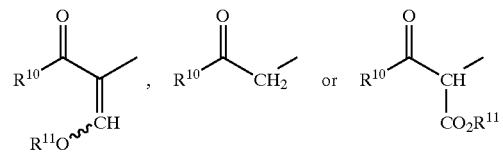

in which $R^1$, $R^2$, $R^{10}$, $R^{11}$, m, n, $T^1$ and M have the same definition as mentioned above.

The reaction of the above-mentioned preparation process a) can be conducted in an appropriate diluent. As examples of such diluents used in that case there can be mentioned aliphatic, alicyclic and aromatic hydrocarbons (which may optionally be chlorinated), for example, toluene, dichloromethane, chloroform or 1,2-dichloroethane; ethers, for example, ethyl ether, dimethoxyethane (DME) or tetrahydrofuran (THF); ketones, for example, methyl isobutyl ketone (MIBK); nitriles, for example, acetonitrile; esters, for example, ethyl acetate; acid amides, for example, dimethylformamide (DMF).

The preparation process a) can be conducted in the presence of a cyanide and a base. As a cyanide employable in that case there can be mentioned, for example, sodium cyanide, potassium cyanide, acetone cyanohydrin or hydrogen cyanide. As a base there can be mentioned, for example, as inorganic bases, hydroxides, carbonates etc. of alkali metals and alkaline earth metals, for example, sodium carbonate, potassium carbonate, lithium hydroxide, sodium hydroxide, potassium hydroxide or calcium hydroxide; and as organic bases, tetiary amines, dialkylaminoanilines and pyridines, for example, triethylamine, pyridine, 4-dimethylaminopyridine (DMAP), 1,4-diazabicyclo[2,2,2] octane (DABCO) or 1,8-diazabicyclo[5,4,0]undec-7-ene (DBU).

The above-mentioned preparation process a) can be conducted also by adding a phase-transfer catalyst to the reaction mixture. As examples of the phase-transfer catalyst employable in that case there can be mentioned crown ethers, for example, dibenzo-18-crown-6, 18-crown-6, 15-crown-5.

The preparation process a) can be conducted in a substantially wide range of temperatures. Suitable temperatures are in the range of generally about −10 to about 80° C., preferably about 5 to about 40° C. Said reaction is conducted desirably under normal pressure. Optionally, however, it is possible to conduct it under elevated pressure or under reduced pressure.

In conducting the preparation process a) the aimed compounds of the above-mentioned general formula (I), in case that Q represents groups (Q-1) or (Q-2), can be obtained, for example, by reacting 1 mole of a compound of the general formula (II) with 1 to 4 moles of triethylamine in a diluent, for example, acetonitrile, in the presence of 0.01 to 0.5 moles of acetonecyanohydrin.

The reaction of the above-mentioned preparation process b) can be conducted in an appropriate diluent. As examples of such diluents used in that case there can be mentioned ethers, for example; dioxane, tetrahydrofuran (THF); alcohols, for example, tert-amyl alcohol or tert-butyl alcohol.

The preparation process b) can be conducted in the presence of a base. As a base employable in that case there can be as inorganic bases, carbonates of alkali metals, for example, sodium carbonate or potassium carbonate; and as organic bases, tertiary amines, for example, triethylamine, pyridine or 4-dimethylamino-pyridine (DMAP).

The preparation process b) can be conducted in a substantially wide range of temperatures. Suitable temperatures are in the range of generally about 5 to about 200° C., preferably about 25 to about 130° C. Said reaction is conducted desirably under normal pressure. Optionally, however, it is possible to conduct it under elevated pressure or under reduced pressure.

In conducting the preparation process b) the aimed compounds of the aforementioned general formula (I), in case that Q represents group (Q-2), can be obtained by reacting 1 mole of a compound of the general formula (II) with 0.5 to 2 moles of potassium carbonate in a diluent, for example, dioxane.

The reaction of the above-mentioned preparation process c) can be conducted in an appropriate diluent. As examples of such diluents used in that case there can be mentioned aliphatic, alicyclic and aromatic hydrocarbons (which may optionally be chlorinated), for example, toluene, dichloromethane, chloroform or 1,2-dichloroethane; ethers, for example, tetrahydrofuran (THF); nitriles, for example, acetonitrile; alcohols, for example, methanol, ethanol or isopropanol.

The preparation process c) can be conducted in the presence of a base. As a base employable in that case there can be mentioned, as inorganic bases, acetates, carbonates, bicarbontes etc. of alkali metals and alkaline earth metals, for example, sodium acetate, sodium hydrogen carbonate, potassium hydrogen carbonate, sodiun carbonate or potassium carbonate; and as organic bases, tertiary amines, dialkylaminoanilines and pyridines, for example, triethylamine, pyridine or 4-dimethylaminopyridine (DMAP).

The preparation process c) can be conducted in a substantially wide range of temperatures. Suitable temperatures are in the range of generally about −10 to about 100° C., preferably about 0 to about 50° C. Said reaction is conducted desirably under normal pressure. Optionally, however, it is possible to conduct it under elevated pressure or under reduced pressure.

In conducting the preparation process c) the aimed compounds of the general formula (I), in case that Q represents group (Q-3) can be obtained, for example, by reacting 1 mole of a compound of the general formula (III) with 1 to 1.5 moles of hydroxylamine hydrochloride in a diluent, for example, ethanol in the presence of 1 to 1.5 moles of sodium acetate.

The reaction of the above-mentioned preparation process d) can be conducted in an appropriate diluent. As examples of such diluents used in that case there can be mentioned water; aliphatic, alicyclic and aromatic hydrocarbons (which may optionally be chlorinated), for example, benzene, toluene, xylene, dichloromethane, chloroform, carbon tetrachloride or 1,2-dichloroethane; ethers, for example, ethyl ether, dioxane, dimethoxyethane (DME) or tetrahydrofuran (THF); nitrites, for example, acetonitrile; alcohols, for example, methanol, ethanol or isopropanol; esters, for example, ethyl acetate; acid amides, for example, dimethylformamide (DMF).

The preparation process d) can be conducted in the presence of a base. As a base employable in that case there can be mentioned, as inorganic bases, hydroxides, carbonates etc. of alkali metals and alkaline earth metals, for example, sodiun carbonate, potassium carbonate, lithium hydroxide, sodium hydroxide, potassium hydroxide or calcium hydroxide; and as organic bases, alcoholates, tertiary amines, dialkylaminoanilines and pyridines, for example, triethylamine, 1,1,4,4-tetramethylethylenediamine (TMEDA) or 4-dimethylaminopyridine (DMAP).

The preparation process d) can be conducted in a substantially wide range of temperatures. Suitable temperatures are in the range of generally about −10 to about 100° C., preferably about 0 to about 50° C. Said reaction is conducted desirably under normal pressure. Optionally, however, it is possible to conduct it under elevated pressure or under reduced pressure.

In conducting the preparation process d) the aimed compounds of the aforementioned general formula (I), in case Q represents group (Q-4), can be obtained, for example, by opening the ring of 1 mole of a compound of the general formula (Ib) in a diluent, for example, dichloromethane in the presence of 1 to 3 moles of triethylamine.

In conducting the preparation process a) the compounds of the general formula (I) can be obtained by starting from a compound of the general formula (VI) and continuously reacting without isolating the compounds of the general formula (IV) and the compounds of the general formula (II). And in the preparation process b) the compounds of the general formula (I) can be also obtained by starting from a compound of the general formula (VI) and continuously reacting without isolating the compounds of the general formula (IV) and the compounds of the general formula (II). In conducting the preparation process c) the compounds of the general formula (I) can be obtained by starting from a compounds of the general formula (IV) and continuously reacting without isolating the compounds of the general formula (XV) to obtain the compound of the general formula (XIII), and then by starting from a compounds of the general formula (XIII) and continuously reacting without isolating the compounds of the general formula (III).

The active compounds of the aforementioned general formula (I), according to the present invention, show, as shown in the biological test examples to be described later, excellent herbicidal activities against various weeds and can be used as herbicides. In the present specification weeds mean, in the broadest sense, all plants which grow in locations where they are undesired.

The compounds of the present invention act as total or selective herbicides depending upon the applied concentration. The active compounds, according to the present invention, can be used, for example, between the following weeds and cultures.

Dicotyledon weeds of the genera: Sinapis, Lepidium, Galium, Stellaria, Chenopodium, Urtica, Senecio, Amaranthus, Portulaca, Xanthium, Ipomoea, Polygonum, Ambrosia, Cirsium, Sonchus, Solanum, Rorippa, Lamium, Veronica, Datura, Viola, Galeopsis, Papaver, Centaurea, Galinsoga, Rotala, Lindemia etc.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cucurbita etc.

Monocotyledon weeds of the genera: Echinochloa, Setaria, Panicum, Digitaria, Phleum, Poa, Festuca, Eleusine, Lolium, Bromus, Avena, Cyperus, Sorghum, Agropyron, Monochoria, Fimbristylis, Sagittaria, Eleocharis, Scirpus, Paspalum, Ischaemum, Agrostis, Alopecurus, Cynodon etc.

Monocotyledon cultures of the genera Oryza, Zea, Triticum, Hordeum, Avena, Secale, Sorghum, Panicum, Saccharum, Ananas, Asparagus, Allium etc.

The use of the compounds, according to the present invention, is not restricted to the above-mentioned plants, but may be applied to other plants in the same manner. The active compounds, according to the present invention, can, depending upon the applied concentration, non-selectively control weeds and may be used, for example, on industrial terrain, rail tracks, paths, places with or without tree plantings. Moreover, the active compounds, according to the present invention, can be used for controlling weeds in perennial cultures and applied in, for example, afforestations, decorative tree plantings, orchards, vineyards, citrus groves, nut orchards, banana plantations, coffee plantations, tea plantations, rubber plantations, oil palm plantations, cocoa plantations, soft fruit plantings, hopfields and can be applied also for the selective controlling of weeds in annual cultures.

According to the invention all plants and plant parts can be treated. The tenn plants includes all plants and plant populations, such as desired or undesired wild plants and cultivated plants (including naturally occurring cultivated varieties). Cultivated plants can be plant varieties that were obtained by conventional breeding and optimizing processes or by biotechnological and genetic engineering methods or a combination of such processes and methods, including transgenic plants and including plant varieties that cannot or can be protected by plant patents or plant variety rights. Plant parts are all parts and organs of plants occurring above or below the surface of the soil, e.g. shoots, leaves, needles, stalks and stems, trunks, flowers, Suits and seeds as well as roots, tubers, bulbs and rhizomes. The term plants parts also includes harvested crops and propagation material, e.g. cuttings, tubers, bulbs, rhizomes, shoots and seeds.

According to the invention the plants and plants parts are treated using the usual methods by applying the active ingredients or compositions containing them directly to the plants or plant parts or to their surroundings (including the soil) or storeroom, e.g. by dipping, spraying, dusting, fogging, spreading and in the case of propagation material also by coating using one or multiple layers.

The active compounds, according to the present invention, can be made into customary formulations. As such formulations there can be mentioned, for example, solutions, wettable powders, emulsions, suspensions, powders, water-dispersible granules, tablets, granules, suspension-emulsion concentrates, microcapsules in polymeric substances or jumbo formulations.

These formulations can be prepared according to per se known methods, for example, by mixing the active compounds with extenders, namely liquid or solid diluents or carriers, and optionally with surface-active agents, namely emulsifiers and/or dispersants and/or foam-forming agents.

As liquid diluents or carriers there can be mentioned, for example, aromatic hydrocarbons (for example, xylene, toluene, alkylnaphthalene), chlorinated aromatic or chlorinated aliphatic hydrocarbons (for example, chlorobenzenes, ethylene chlorides, methylene chloride), aliphatic hydrocarbons (for example, cyclohexane or paraffins (for example, mineral oil fractions)), alcohols (for example, butanol, glycol) and their ethers, esters etc., ketones (for example, acetone, methyl ethyl ketone, methyl isobutyl ketone or cyclohexanone), strongly polar solvents (for example, dimethylformamide, dimethyl sulphoxide) and water. In case of using water as an extender, for example, organic solvents can be used as auxiliary solvents.

As solid diluents or carriers there can be mentioned, for example, ground natural minerals (for example, kaolin, clay, talc, chalk, quartz, attapulgite, montmorillonite, diatomaceous earth) or ground synthetic minerals (for example, highly dispersed silicic acid, alumina, silicates). As solid carriers for granules there can be mentioned, for example, crushed and fractionated rocks (for example, calcite, marble, pumice, sepiolite, dolomite), synthetic granules of inorganic and organic meals or particles of organic material (for example, sawdust, coconut shells, maize cobs and tobacco stalks).

As emulsifiers and/or foam-forming agents there can be mentioned, for example, nonionic and anionic emulsifiers [for example, polyoxyethylene fatty acid esters or polyoxyethylene fatty acid alcohol ethers (for example, alkylaryl polyglycol ethers, alkylsulphonates, alkylsulphates, arylsulphonates)]and albumin hydrolysis products.

As dispersants there are included, for example, ligninsulphite waste liquor and methyl cellulose.

Tackifiers may also be used in formulations (powders, granules, emulsions). As said tackifiers there can be mentioned, for example, carboxymethyl cellulose, natural and synthetic polymers (for example, gum arabic, polyvinyl alcohol, polyvinyl acetate).

Colorants may also be used. As said colorants there can be mentioned inorganic pigments (for example, iron oxide, titanium oxide, Prussian Blue) and organic dyestuffs such as alizarin dyestuffs, azo dyestuffs or metal phthalocyanine dyestuffs, and further trace nutrients such as salts of metals such as iron, manganese, boron, copper, cobalt, molybdenum, zinc.

Said formulations can contain in a range of generally 0.1 to 95% by weight, preferably 0.5 to 90% by weight of the active compounds of the general formula (I).

The active compounds of the general formula (I), according to the present invention, can be used as such or in form of their formulation for controlling weeds. They can be used also as a mixed agent with other known herbicides. Such a mixed agent can be previously prepared as a form of final formulation or can be prepared by tank-mixing on occasion of the application. As a possible mixing partner in such combinations there can be mentioned, for example, known herbicides such as sulfonylurea type herbicides for paddy field use.

Furthermore, the active compounds of the general formula (I), according to the present invention, can be mixed also with a safener and their application as a selective herbicide may be broadened by such a mixing. As an example of such safener 1-(α,α-dimethylbenzyl)-3-p-tolylurea can be mentioned.

Surprisingly, some of the combinations of the compounds according to the present invention with other mixing partners show synergistic effects.

In case of using the active compounds of the general formula (I), according to the present invention, they can be directly used as such or in form of formulations such as ready-to-use solutions, emulsions, tablets, suspensions, powders, pastes, granules or used in the use forms prepared by further dilution. The active compounds, according to the present invention, can be applied by means of, for example, watering, spraying, atomizing or granule application.

The active compounds of the general formula (I), according to the present invention, can be used at any stages before and after germination of plants. They may also be applied to the soil before sowing.

The application rates of the active compounds, according to the present invention, may be varied in a substantial range and are fundamentally different according to the nature of the desired effect. In case of herbicidal use, as the application rate there can be mentioned, for example, ranges of about 0.01 to about 4 kg, preferably about 0.05 to about 3 kg of the active compounds per hectare.

The preparation and fields of application of the compounds according to the present invention will be described more specifically by the following examples. However, the present invention should not be restricted to them in any way.

SYNTHESIS EXAMPLE 1

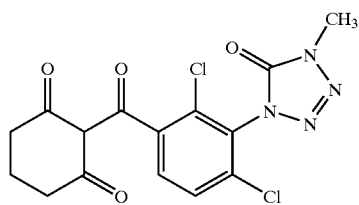

2,4-Dichloro-3-(4,5-dihydro-4-methyl-5-oxo-1H-tetrazol-1-yl)benzoic acid (3.42 g) and thionylchloride (4.22 g) were added to 1,2-dichloroethane (50 ml). The mixture, after adding several drops of N,N-dimethylformamide, was refluxed upon heating for 4 hours. After cooling, the solvent was distilled off to obtain crude 2,4-dichloro-3-(4,5-dihydro-4-methyl-5-oxo-1H-tetrazol-1-yl)benzoyl chloride (3.65 g).

A dichloromethane solution of the crude 2,4-dichloro-3-(4,5-dihydro-4-methyl-5-oxo-1H-tetrazol-1-yl)benzoyl chloride (1.10 g) was added drop by drop to the solution of 1,3-cyclohexanedione (0.44 g) and triethylamine (0.43 g) in dichloro-methane (8 ml) at 5° C. and the mixture was stirred at room temperature for 6 hours. After completion of the reaction it was extracted with dichloromethane (150 ml), washed with diluted hydrochloric acid and aqueous solution of sodium hydrogen carbonate and then dried with anhydrous magnesium sulfate. The residue, obtained by distilling off the dichloromethane, was dissolved in acetonitrile (7 ml), added with triethylamine (0.43 g) and acetonecyanohydrin (18 mg) and stirred at room temperature for 8 hours. After the solvent was distilled off, the residue was acidified by addition of diluted hydrochloric acid and extracted with ethyl acetate (150 ml). The organic layer was washed with saturated salt water and dried with anhydrous magnesium sulfate. By distilling off the ethyl acetate, the objective 2-[2,4-dichloro-3-(4,5-dihydro-4-methyl-5-oxo-1H-tetrazol-1-yl )benzoyl]cyclohexan-1,3-dione (0.70g, 51% yield from 2,4-dichloro-3-(4,5-dihydro-4-methyl-5-oxo-1H-tetrazol-1-yl)benzoic acid) was obtained. mp 138–140° C.

SYNTHESIS EXAMPLE 2

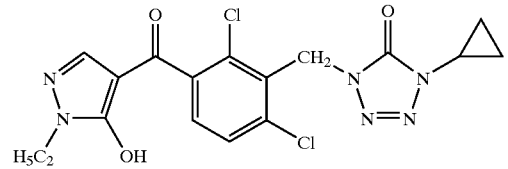

3-[(4Cyclopropyl-4,5-dihydro-5-oxo-1H-tetrazol-1-yl)methyl]-2,4-dichlorobenzoic acid (5.05 g) and thionyl chloride (5.48 g) were added to 1,2-dichloroethane (60 ml) and the mixture, after adding several drops of DMF, was refluxed upon heating. After cooling, the solvent was distilled off to obtain crude 3-[(4-cyclopropyl-4,5-dihydro-5-oxo-1H-tetrazol-1-yl)methyl]-2,4-dichlorobenzoyl chloride (5.46 g).

A 1,2-dichloroethane solution of 3-[(4-cyclopropyl-4,5-dihydro-5-oxo-1H-tetrazol-1-yl)methyl]-2,4-dichlorobenzoyl chloride (0.70g) was added drop by drop to the solution of 1-ethyl-5-hydroxypyrazole (0.24 g) and triethylamine (0.24 g) in 1,2-dichloroethane (4 ml) at 5° C. and the mixture was stirred at room temperature for 6 hours. After reaction it was extracted with dichloromethane (100 ml), washed with diluted hydrochloric acid and aqueous solution of sodium hydrogen carbonate and then dried with anhydrous magnesium sulfate. The residue, obtained by distilling off the solvent, was dissolved in 1,4-dioxane (8 ml), added with potassium carbonate (0.38 g) and refluxed by heating for 3 hours. After the solvent was distilled off, the residue was teated with an aqueous solution of potassium carbonate and washed with ethyl acetate. The aqueous layer was acidified with hydrochloric acid and extracted with ethyl acetate (150 ml). The organic layer was washed with saturated salt water and dried with anhydrous magnesium sulfate. By distilling off the ethyl acetate, the objective 4-{3-[(4-cyclopropyl-4,5-dihydro-5-oxo-1H-tetrazol-1-yl)methyl]-2,4-dichlorobenzoyl}-5-hydroxy-1-ethylpyrazole (0.73 g, 88% yield from 3-[(4-cyclopropyl-4,5-dihydro-5-oxo-1H-tetrazol-1-yl) methyl]-2,4-dichlorobenzoic acid) was obtained. $n_D^{20}$: 1.5510.

SYNTHESIS EXAMPLE 3

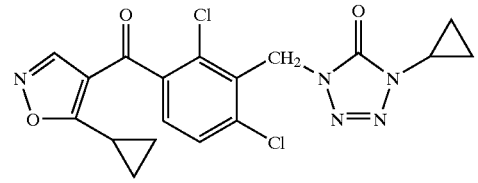

3-Cyclopropyl-1-{3-[(4-cyclopropyl-4,5-dihydro-5-oxo-1H-tetrazol-1-yl)methyl]-2,4-dichlorophenyl}propan-1,3-dione (2.64 g) was dissolved in acetic anhydride (15 ml) and the solution, after adding triethyl orthoformate (2.12 g), was refluxed for 4 hours upon heating. The solvent was distilled off under reduced pressure and the residue was treated with toluene, which was distilled off under reduced pressure to obtain crude 3-cyclopropyl-1-{3-[(4-cyclopropyl-4,5-dihydro-5-oxo-1H-tetrazol-1-yl)methyl]-2,4-dichlorophenyl}-2-ethoxymethylenepropan-1,3-dione (3.23 g).

To a mixture of 3-cyclopropyl-1-{3-[(4-cyclopropyl-4,5-dihydro-5-oxo-1H-tetrazol-1-yl)methyl]-2,4-dichlorophenyl}-2-ethoxymethylenepropan-1,3-dione (3.22 g) and hydroxylamine hydrochloride (0.54 g) in ethanol (15 ml), sodium acetate (0.62 g) was added in several portions while stirring and the mixture was stirred at room temperature for 6 hours. The solvent was distilled off the mixture under reduced pressure and the residue was extracted with ethyl acetate (120 ml), washed with salt water and dried with anhydrous magnesium sulfate. The residue, obtained by distilling off the ethyl acetate, was purified by silica column chromatography (ethyl acetate: n-hexane=1:1) to obtain the objective 5-cyclopropyl-4-{3-[(4-cyclopropyl-4,5-dihydro-5-oxo-1H-tetrazol-1-yl)methyl]-2,4-dichlorobenzoyl}isoxazole (2.37 g, 84% yield from 3-cyclopropyl-1-{3-[(4-cyclopropyl-4,5-dihydro-5-oxo-1H-tetrazol-1-yl)methyl]-2,4-dichlorophenyl}propan-1,3-dione. $n_D^{20}$ : 1.5929.

SYNTHESIS EXAMPLE 4

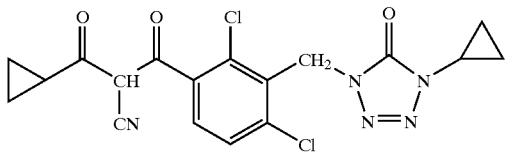

5-Cyclopropyl-4-{3-[(4-cyclopropyl-4,5-dihydro-5-oxo-1H-tetrazol-1-yl)methyl]-2,4-dichlorobenzoyl}isoxazole (1.30 g) was dissolved in dichloromethane (10 ml) and the solution, after adding triethylamine (0.50 g) drop by drop, was stirred at room temperature for 6 hours.

The reaction solution was acidified by adding 2N hydrochloric acid, extracted with dichloromethane (100 ml), washed with salt water and dried with anhydrous magnesium sulfate. By distilling off the dichloromethane the objective 2-cyano-3-cyclopropyl-1-{3-[(4-cyclopropyl-4,5-dihydro-5-oxo-1H-tetrazol-1-yl)methyl]-2,4-dichlorophenyl}propan-1,3-dione (1.30 g, quantitative yield) was obtained. mp: 129–132° C.

The compounds, obtained in the same manner as described in the above-mentioned Synthesis Examples 1 to 4, are shown in the following Tables 1 to 3, together with the compounds synthesized in the Synthesis Examples 1 to 4.

In Tables 1, 2 and 3

Q1 represents the group

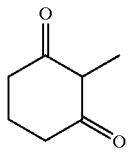

Q2 represents the group

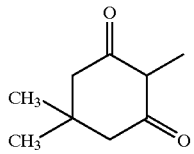

Q3 represent the group

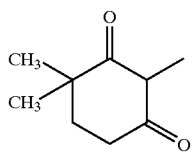

Q4 represent the group

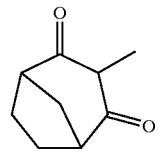

Q5 represents the group

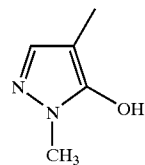

Q6 represents the group

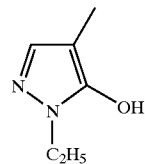

Q7 represents the group

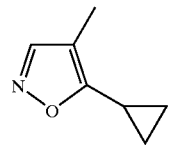

Q8 represents the group

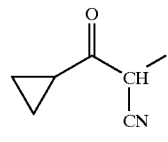

Q9 represents the group

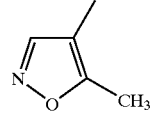

Q10 represents the group

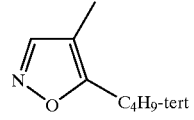

and,

Q11 represents the group

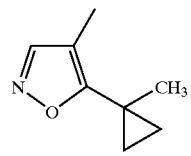

TABLE 1
| Compound No. | Y | Z | R² | n | Q | Property ($n_{20}^D$ or mp. ° C.) |
|---|---|---|---|---|---|---|
| 1. | H | H | CH₃ | 0 | Q1 | 1.5923 |
| 2. | H | H | CH₃ | 0 | Q4 | |
| 3. | H | H | CH₃ | 0 | Q6 | |
| 4. | H | H | CH₃ | 1 | Q1 | |
| 5. | H | H | CH₃ | 1 | Q5 | |
| 6. | H | H | CH₃ | 1 | Q7 | |
| 7. | OCH₃ | H | CH₃ | 0 | Q1 | |
| 8. | OCH₃ | H | CH₃ | 1 | Q1 | |
| 9. | Cl | H | CH₃ | 0 | Q1 | |
| 10. | Cl | H | CH₃ | 1 | Q1 | |
| 11. | CH₃ | H | CH₃ | 1 | Q1 | |
| 12. | H | F | CH₃ | 0 | Q1 | |
| 13. | H | F | CH₃ | 0 | Q4 | |
| 14. | H | F | CH₃ | 0 | Q6 | |
| 15. | H | F | CH₃ | 0 | Q7 | |
| 16. | H | F | CH₃ | 1 | Q1 | |
| 17. | H | F | CH₃ | 1 | Q2 | |
| 18. | H | F | CH₃ | 1 | Q4 | |
| 19. | H | F | CH₃ | 1 | Q5 | |
| 20. | H | F | CH₃ | 1 | Q7 | |
| 21. | H | F | C₂H₅ | 0 | Q1 | |
| 22. | H | F | C₂H₅ | 0 | Q8 | |
| 23. | H | F | C₂H₅ | 1 | Q1 | |
| 24. | H | F | C₂H₅ | 1 | Q3 | |
| 25. | H | F | C₂H₅ | 1 | Q4 | |
| 26. | H | F | C₂H₅ | 1 | Q6 | |
| 27. | H | F | C₂H₅ | 1 | Q7 | |
| 28. | H | F | n-C₃H₇ | 1 | Q1 | |
| 29. | H | F | n-C₃H₇ | 1 | Q5 | |
| 30. | H | F | iso-C₃H₇ | 1 | Q1 | |
| 31. | H | F | iso-C₃H₇ | 1 | Q6 | |
| 32. | H | F |  | 1 | Q1 | |
| 33. | H | F | 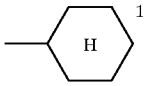 | 1 | Q7 | |
| 34. | H | F | 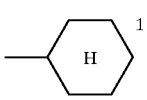 | 1 | Q1 | |
| 35. | H | F | 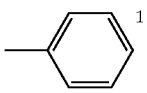 | 1 | Q8 | |
| 36. | H | F | 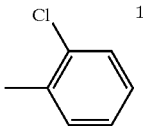 | 1 | Q1 | |
| 37. | H | F |  | 1 | Q1 | |
| 38. | H | F | CHF₂ | 0 | Q1 | |
| 39. | H | F | CHF₂ | 0 | Q4 | |

TABLE 1-continued

| Compound No. | Y | Z | R² | n | Q | Property ($n_{20}^D$ or mp. °C.) |
|---|---|---|---|---|---|---|
| 40. | H | F | CH₂CH₂CH₂F | 0 | Q1 | |
| 41. | H | F | CH₂CH₂CH₂F | 0 | Q5 | |
| 42. | H | F | CH₂CF₃ | 1 | Q1 | |
| 43. | H | F | CH₂CF₃ | 1 | Q6 | |
| 44. | H | F | CH₂CF₂CF₃ | 1 | Q1 | |
| 45. | H | Cl | CH₃ | 0 | Q1 | |
| 46. | H | Cl | CH₃ | 0 | Q4 | |
| 47. | H | Cl | CH₃ | 0 | Q6 | |
| 48. | H | Cl | CH₃ | 0 | Q7 | |
| 49. | H | Cl | CH₃ | 1 | Q1 | |
| 50. | H | Cl | CH₃ | 1 | Q2 | |
| 51. | H | Cl | CH₃ | 1 | Q4 | |
| 52. | H | Cl | CH₃ | 1 | Q6 | |
| 53. | H | Cl | CH₃ | 1 | Q8 | |
| 54. | H | Cl | C₂H₅ | 0 | Q1 | |
| 55. | H | Cl | C₂H₅ | 0 | Q7 | |
| 56. | H | Cl | C₂H₅ | 1 | Q1 | |
| 57. | H | Cl | C₂H₅ | 1 | Q2 | |
| 58. | H | Cl | C₂H₅ | 1 | Q4 | |
| 59. | H | Cl | C₂H₅ | 1 | Q6 | |
| 60. | H | Cl | C₂H₅ | 1 | Q7 | |
| 61. | H | Cl | n-C₃H₇ | 1 | Q1 | |
| 62. | H | Cl | n-C₃H₇ | 1 | Q6 | |
| 63. | H | Cl | iso-C₃H₇ | 1 | Q1 | |
| 64. | H | Cl | iso-C₃H₇ | 1 | Q7 | |
| 65. | H | Cl |  | 1 | Q1 | |
| 66. | H | Cl |  | 1 | Q8 | |
| 67. | H | Cl | 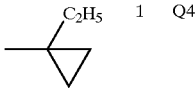 | 1 | Q4 | |
| 68. | H | Cl | 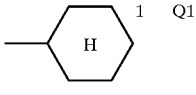 | 1 | Q1 | |
| 69. | H | Cl | 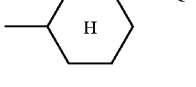 | 1 | Q4 | |
| 70. | H | Cl | 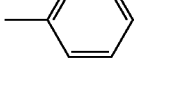 | 1 | Q1 | |
| 71. | H | Cl | 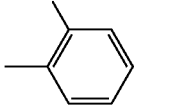 | 1 | Q1 | |
| 72. | H | Cl | CHF₂ | 0 | Q1 | |
| 73. | H | Cl | CHF₂ | 0 | Q5 | |
| 74. | H | Cl | CH₂CH₂CH₂F | 0 | Q1 | |

TABLE 1-continued
| Compound No. | Y | Z | R² | n | Q | Property ($n_{20}^D$ or mp. °C.) |
|---|---|---|---|---|---|---|
| 75. | H | Cl | CH₂CH₂CH₂F | 0 | Q6 | |
| 76. | H | Cl | CH₂CF₃ | 1 | Q1 | |
| 77. | H | Br | CH₃ | 0 | Q1 | |
| 78. | H | Br | CH₃ | 0 | Q4 | |
| 79. | H | Br | CH₃ | 0 | Q6 | |
| 80. | H | Br | CH₃ | 0 | Q7 | |
| 81. | H | Br | CH₃ | 1 | Q1 | 134–141 |
| 82. | H | Br | CH₃ | 1 | Q3 | |
| 83. | H | Br | CH₃ | 1 | Q4 | |
| 84. | H | Br | CH₃ | 1 | Q6 | 112–115 |
| 85. | H | Br | CH₃ | 1 | Q8 | |
| 86. | H | Br | C₂H₅ | 0 | Q1 | |
| 87. | H | Br | C₂H₅ | 0 | Q6 | |
| 88. | H | Br | C₂H₅ | 1 | Q1 | |
| 89. | H | Br | C₂H₅ | 1 | Q2 | |
| 90. | H | Br | C₂H₅ | 1 | Q4 | |
| 91. | H | Br | C₂H₅ | 1 | Q5 | |
| 92. | H | Br | C₂H₅ | 1 | Q8 | |
| 93. | H | Br | C₃H₇-n | 1 | Q1 | |
| 94. | H | Br | C₃H₇-n | 1 | Q7 | |
| 95. | H | Br | C₃H₇-iso | 1 | Q1 | |
| 96. | H | Br | C₃H₇-iso | 1 | Q8 | |
| 97. | H | Br |  | 1 | Q1 | |
| 98. | H | Br |  | 1 | Q4 | |
| 99. | H | Br | 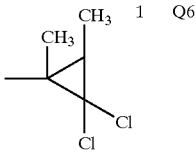 | 1 | Q1 | |
| 100. | H | Br | 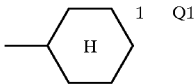 | 1 | Q6 | |
| 101. | H | Br | 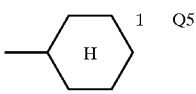 | 1 | Q1 | |
| 102. | H | Br | 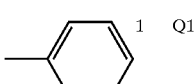 | 1 | Q5 | |
| 103. | H | Br |  | 1 | Q1 | |

TABLE 1-continued

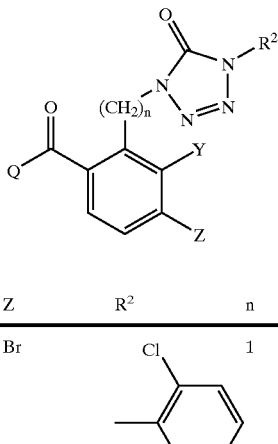

| Compound No. | Y | Z | R² | n | Q | Property ($n_{20}^D$ or mp. ° C.) |
|---|---|---|---|---|---|---|
| 104. | H | Br |  | 1 | Q1 | |
| 105. | H | Br | CHF₂ | 0 | Q1 | |
| 106. | H | Br | CHF₂ | 0 | Q6 | |
| 107. | H | Br | CH₂CH₂CH₂F | 0 | Q1 | |
| 108. | H | Br | CH₂CH₂CH₂F | 0 | Q7 | |
| 109. | H | Br | CH₂CF₂CF₃ | 1 | Q1 | |
| 110. | H | I | CH₃ | 0 | Q1 | |
| 111. | H | I | CH₃ | 0 | Q6 | |
| 112. | H | I | CH₃ | 1 | Q1 | |
| 113. | H | I | CH₃ | 1 | Q6 | |
| 114. | H | CH₃ | CH₃ | 0 | Q1 | |
| 115. | H | CH₃ | CH₃ | 0 | Q6 | |
| 116. | H | CF₃ | CH₃ | 0 | Q1 | |
| 117. | H | CF₃ | CH₃ | 0 | Q4 | |
| 118. | H | CF₃ | CH₃ | 0 | Q5 | |
| 119. | H | CF₃ | CH₃ | 0 | Q6 | |
| 120. | H | CF₃ | CH₃ | 0 | Q7 | |
| 121. | H | CF₃ | CH₃ | 1 | Q1 | 1.5313 |
| 122. | H | CF₃ | CH₃ | 1 | Q2 | |
| 123. | H | CF₃ | CH₃ | 1 | Q3 | |
| 124. | H | CF₃ | CH₃ | 1 | Q4 | |
| 125. | H | CF₃ | CH₃ | 1 | Q5 | |
| 126. | H | CF₃ | CH₃ | 1 | Q6 | |
| 127. | H | CF₃ | CH₃ | 1 | Q7 | |
| 128. | H | CF₃ | CH₃ | 1 | Q8 | |
| 129. | H | CF₃ | C₂H₅ | 0 | Q1 | |
| 130. | H | CF₃ | C₂H₅ | 0 | Q8 | |
| 131. | H | CF₃ | C₂H₅ | 1 | Q1 | |
| 132. | H | CF₃ | C₂H₅ | 1 | Q3 | |
| 133. | H | CF₃ | C₂H₅ | 1 | Q4 | |
| 134. | H | CF₃ | C₂H₅ | 1 | Q6 | |
| 135. | H | CF₃ | C₂H₅ | 1 | Q7 | |
| 136. | H | CF₃ | C₃H₇-n | 1 | Q1 | |
| 137. | H | CF₃ | C₃H₇-n | 1 | Q5 | |
| 138. | H | CF₃ | C₃H₇-iso | 1 | Q1 | |
| 139. | H | CF₃ | C₃H₇-iso | 1 | Q6 | |
| 140. | H | CF₃ |  | 1 | Q1 | |
| 141. | H | CF₃ |  | 1 | Q7 | |
| 142. | H | CF₃ | 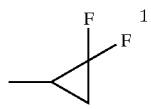 C₃H₇-n | 1 | Q5 | |
| 143. | H | CF₃ |  | 1 | Q1 | |

TABLE 1-continued

[Structure: benzoic acid derivative with tetrazolinone substituent, showing Q-C(=O)-O group, (CH₂)ₙ linker to N of tetrazolinone ring with R² on other N, and Y, Z substituents on benzene ring]

| Compound No. | Y | Z | R² | n | Q | Property ($n_{20}^D$ or mp. °C.) |
|---|---|---|---|---|---|---|
| 144. | H | CF₃ | cyclohexyl-H | 1 | Q1 | |
| 145. | H | CF₃ | cyclohexyl-H | 1 | Q8 | |
| 146. | H | CF₃ | phenyl | 1 | Q1 | |
| 147. | H | CF₃ | 2-Cl-phenyl | 1 | Q1 | |
| 148. | H | CF₃ | CHF₂ | 0 | Q1 | |
| 149. | H | CF₃ | CHF₂ | 0 | Q4 | |
| 150. | H | CF₃ | CH₂CH₂CH₂F | 0 | Q1 | |
| 151. | H | CF₃ | CH₂CH₂CH₂F | 0 | Q5 | |
| 152. | H | CF₃ | CH₂CF₃ | 1 | Q1 | |
| 153. | H | CF₃ | CH₂CF₃ | 1 | Q6 | |
| 154. | H | CF₃ | CH₂CF₃ | 1 | Q7 | |
| 155. | H | CF₃ | CH₂CF₂CF₃ | 1 | Q1 | |
| 156. | H | OCH₃ | CH₃ | 0 | Q1 | |
| 157. | H | OCH₃ | CH₃ | 0 | Q6 | |
| 158. | H | OCH₃ | CH₃ | 1 | Q1 | |
| 159. | H | OSO₂CH₃ | CH₃ | 0 | Q1 | |
| 160. | H | OSO₂CH₃ | CH₃ | 1 | Q1 | |
| 161. | H | OSO₂CH₃ | CH₃ | 1 | Q6 | |
| 162. | H | SCH₃ | CH₃ | 0 | Q1 | |
| 163. | H | SCH₃ | CH₃ | 1 | Q1 | |
| 164. | H | SO₂CH₃ | CH₃ | 0 | Q1 | |
| 165. | H | SO₂CH₃ | CH₃ | 1 | Q1 | |
| 166. | H | SO₂CH₃ | CH₃ | 1 | Q6 | |
| 167. | H | SO₂CH₃ | C₂H₅ | 0 | Q1 | |
| 168. | H | SO₂CH₃ | C₂H₅ | 1 | Q1 | |
| 169. | H | SO₂CH₃ | C₂H₅ | 1 | Q7 | |
| 170. | H | SO₂CH₃ | C₃H₇-iso | 0 | Q1 | |
| 171. | H | SO₂CH₃ | C₃H₇-iso | 1 | Q1 | |
| 172. | H | SO₂CH₃ | C₃H₇-iso | 1 | Q8 | |
| 173. | H | SO₂CH₃ | cyclopropyl | 1 | Q1 | |
| 174. | H | SO₂CH₃ | cyclopropyl | 1 | Q4 | |
| 175. | H | SO₂CH₃ | cyclohexyl-H | 1 | Q1 | |
| 176. | H | NO₂ | CH₃ | 0 | Q1 | |
| 177. | H | NO₂ | CH₃ | 0 | Q6 | |
| 178. | H | NO₂ | CH₃ | 0 | Q7 | |

TABLE 1-continued

| Compound No. | Y | Z | R² | n | Q | Property (n₂₀ᴅ or mp. °C.) |
|---|---|---|---|---|---|---|
| 179. | H | NO₂ | CH₃ | 1 | Q1 | 1.5855 |
| 180. | H | NO₂ | CH₃ | 1 | Q5 | |
| 181. | H | NO₂ | CH₃ | 1 | Q6 | |
| 182. | H | NO₂ | CH₃ | 1 | Q7 | |
| 183. | H | NO₂ | C₂H₅ | 0 | Q1 | |
| 184. | H | NO₂ | C₂H₅ | 0 | Q8 | |
| 185. | H | NO₂ | C₂H₅ | 1 | Q1 | |
| 186. | H | NO₂ | C₂H₅ | 1 | Q6 | |
| 187. | H | NO₂ | C₂H₅ | 1 | Q7 | |
| 188. | H | NO₂ | C₃H₇-n | 1 | Q1 | |
| 189. | H | NO₂ | C₃H₇-n | 1 | Q5 | |
| 190. | H | NO₂ | C₃H₇-iso | 1 | Q1 | |
| 191. | H | NO₂ | C₃H₇-iso | 1 | Q6 | |
| 192. | H | NO₂ |  | 1 | Q1 | |
| 193. | H | NO₂ | 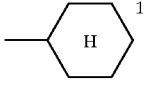 | 1 | Q7 | |
| 194. | H | NO₂ | 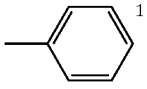 | 1 | Q8 | |
| 195. | H | NO₂ | 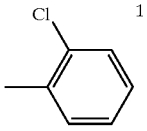 | 1 | Q1 | |
| 196. | H | NO₂ |  | 1 | Q1 | |
| 197. | H | NO₂ | CHF₂ | 0 | Q1 | |
| 198. | H | NO₂ | CHF₂ | 0 | Q4 | |
| 199. | H | NO₂ | CH₂CH₂CH₂F | 0 | Q1 | |
| 200. | H | NO₂ | CH₂CF₃ | 1 | Q1 | |
| 201. | H | CN | CH₃ | 0 | Q1 | |
| 202. | H | CN | CH₃ | 0 | Q6 | |
| 203. | H | CN | CH₃ | 1 | Q1 | |
| 204. | H | CN | CH₃ | 1 | Q6 | |
| 205. | H | CN | C₂H₅ | 0 | Q1 | |
| 206. | H | CN | C₂H₅ | 1 | Q1 | |
| 207. | H | CN |  | 1 | Q1 | |
| 208. | H | CN |  | 1 | Q6 | |
| 209. | CO₂CH₃ | Cl | CH₃ | 1 | Q1 | |
| 210. | CO₂CH₃ | Cl | CH₃ | 1 | Q6 | |
| 211. | CO₂CH₃ | Cl | CH₃ | 1 | Q7 | |
| 212. | CO₂CH₃ | SCH₃ | CH₃ | 1 | Q1 | |
| 213. | CO₂CH₃ | SCH₃ | CH₃ | 1 | Q6 | |
| 214. | CO₂CH₃ | SO₂CH₃ | CH₃ | 0 | Q1 | |
| 215. | CO₂CH₃ | SO₂CH₃ | CH₃ | 1 | Q1 | |

TABLE 1-continued

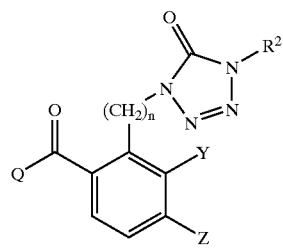

| Compound No. | Y | Z | R² | n | Q | Property ($n_{20}^D$ or mp. °C.) |
|---|---|---|---|---|---|---|
| 216. | $CO_2CH_3$ | $SO_2CH_3$ | $CH_3$ | 1 | Q6 | |
| 217. | $CO_2CH_3$ | $SO_2CH_3$ | $CH_3$ | 1 | Q7 | |
| 218. | $CH_2OCH_3$ | Cl | $CH_3$ | 1 | Q1 | |
| 219. | $CH_2OCH_3$ | Cl | $CH_3$ | 1 | Q6 | |
| 220. | $CH_2OCH_3$ | Cl | $CH_3$ | 1 | Q7 | |
| 221. | $CH_2OCH_3$ | $SCH_3$ | $CH_3$ | 1 | Q1 | |
| 222. | $CH_2OCH_3$ | $SCH_3$ | $CH_3$ | 1 | Q6 | |
| 223. | $CH_2OCH_3$ | $SO_2CH_3$ | $CH_3$ | 1 | Q1 | |
| 224. | $CH_2OCH_3$ | $SO_2CH_3$ | $CH_3$ | 1 | Q6 | |
| 225. | $CH_2OCH_3$ | $SO_2CH_3$ | $CH_3$ | 1 | Q7 | |
| 226. | $CH_2SCH_3$ | Cl | $CH_3$ | 1 | Q1 | |
| 227. | $CH_2SCH_3$ | Cl | $CH_3$ | 1 | Q6 | |
| 228. | $CH_2SCH_3$ | Cl | $CH_3$ | 1 | Q7 | |
| 229. | $CH_2SCH_3$ | $SCH_3$ | $CH_3$ | 1 | Q1 | |
| 230. | $CH_2SCH_3$ | $SCH_3$ | $CH_3$ | 1 | Q6 | |
| 231. | $CH_2SCH_3$ | $SO_2CH_3$ | $CH_3$ | 1 | Q1 | |
| 232. | $CH_2SCH_3$ | $SO_2CH_3$ | $CH_3$ | 1 | Q6 | |
| 233. | $CH_2SCH_3$ | $SO_2CH_3$ | $CH_3$ | 1 | Q7 | |
| 234. | H | $OSO_2C_2H_5$ | $CH_3$ | 1 | Q1 | |
| 235. | H | $OSO_2C_3H_7$-n | $CH_3$ | 1 | Q1 | |
| 236. | H | $OSO_2CH_3$ | $CH_3$ | 1 | Q6 | |

TABLE 2

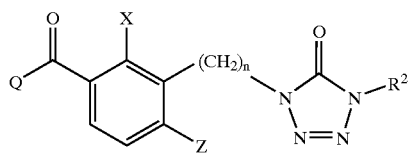

| Compound No. | X | Z | R² | n | Q | Property ($n_{20}^D$ or mp. °C.) |
|---|---|---|---|---|---|---|
| 237. | H | H | $CH_3$ | 0 | Q1 | |
| 238. | H | H | $CH_3$ | 0 | Q5 | |
| 239. | H | H | $CH_3$ | 0 | Q6 | |
| 240. | H | H | $CH_3$ | 1 | Q1 | |
| 241. | H | H | $CH_3$ | 1 | Q5 | |
| 242. | H | H | $CH_3$ | 1 | Q6 | |
| 243. | H | F | $CH_3$ | 0 | Q1 | |
| 244. | H | Cl | $CH_3$ | 0 | Q1 | 136–142 |
| 245. | H | Cl | $CH_3$ | 0 | Q6 | |
| 246. | H | Cl | $CH_3$ | 1 | Q1 | |
| 247. | H | Br | $CH_3$ | 1 | Q1 | |
| 248. | H | $CH_2SO_2CH_3$ | $CH_3$ | 1 | Q1 | |
| 249. | Cl | H | $CH_3$ | 0 | Q1 | amorphous |
| 250. | Br | H | $CH_3$ | 0 | Q1 | |
| 251. | $OCH_3$ | H | $CH_3$ | 0 | Q1 | |
| 252. | $OCH_3$ | H | $CH_2CH_2CH_2F$ | 0 | Q1 | |
| 253. | $OCH_3$ | H | $CH_2CF_3$ | 1 | Q1 | |
| 254. | $OSO_2CH_3$ | H | $CH_3$ | 0 | Q1 | |
| 255. | $OSO_2CH_3$ | H | $CHF_2$ | 0 | Q1 | |
| 256. | $OSO_2CH_3$ | H | $CH_2CF_2CF_3$ | 1 | Q1 | |
| 257. | $OSO_2CH_3$ | H | $CH_3$ | 1 | Q1 | |
| 258. | $NO_2$ | H | $CH_3$ | 0 | Q1 | |
| 259. | $NO_2$ | H | $CH_3$ | 1 | Q1 | |
| 260. | F | Cl | $CH_3$ | 0 | Q1 | |
| 261. | F | Cl | $CH_3$ | 0 | Q6 | |
| 262. | F | Cl | $CH_3$ | 1 | Q1 | 65–70 |

TABLE 2-continued

| Compound No. | X | Z | R² | n | Q | Property ($n_{20}^D$ or mp. °C.) |
|---|---|---|---|---|---|---|
| 263. | F | Cl | CH₃ | 1 | Q6 | |
| 264. | F | Cl | CH₃ | 1 | Q7 | |
| 265. | F | Cl | C₂H₅ | 0 | Q1 | |
| 266. | F | Cl | C₂H₅ | 1 | Q1 | |
| 267. | F | Cl | C₂H₅ | 1 | Q6 | |
| 268. | F | Cl | C₃H₇-n | 1 | Q1 | |
| 269. | F | Cl | C₃H₇-n | 1 | Q6 | |
| 270. | F | Cl | cyclopropyl | 1 | Q1 | 1.5770 |
| 271. | F | Cl | cyclopropyl | 1 | Q4 | amorphous |
| 272. | F | Cl | cyclopropyl | 1 | Q6 | |
| 273. | F | Cl | cyclopropyl | 1 | Q7 | 1.5729 |
| 274. | F | Cl | cyclopropyl | 1 | Q8 | |
| 275. | F | Cl | phenyl | 1 | Q1 | |
| 276. | F | Cl | phenyl | 1 | Q6 | |
| 277. | F | Cl | 2-Cl-phenyl | 1 | Q1 | amorphous |
| 278. | F | Cl | 2-Cl-phenyl | 1 | Q6 | |
| 279. | F | Cl | 2-Cl-phenyl | 1 | Q7 | 147–149 |
| 280. | F | Cl | CHF₂ | 0 | Q1 | |
| 281. | F | Cl | CH₂CH₂CH₂F | 0 | Q1 | |
| 282. | Cl | Cl | CH₃ | 0 | Q1 | 138–140 |
| 283. | Cl | Cl | CH₃ | 0 | Q2 | |
| 284. | Cl | Cl | CH₃ | 0 | Q4 | |
| 285. | Cl | Cl | CH₃ | 0 | Q6 | |
| 286. | Cl | Cl | CH₃ | 0 | Q7 | amorphous |
| 287. | Cl | Cl | CH₃ | 0 | Q8 | 67–69 |
| 288. | Cl | Cl | CH₃ | 1 | Q1 | 163–165 |
| 289. | Cl | Cl | CH₃ | 1 | Q3 | |
| 290. | Cl | Cl | CH₃ | 1 | Q4 | |
| 291. | Cl | Cl | CH₃ | 1 | Q5 | |

TABLE 2-continued

| Compound No. | X | Z | R² | n | Q | Property (n₂₀ᴅ or mp. °C.) |
|---|---|---|---|---|---|---|
| 292. | Cl | Cl | CH₃ | 1 | Q6 | |
| 293. | Cl | Cl | CH₃ | 1 | Q7 | amorphous |
| 294. | Cl | Cl | CH₃ | 1 | Q8 | 129–132 |
| 295. | Cl | Cl | C₂H₅ | 0 | Q1 | |
| 296. | Cl | Cl | C₂H₅ | 0 | Q4 | |
| 297. | Cl | Cl | C₂H₅ | 0 | Q6 | |
| 298. | Cl | Cl | C₂H₅ | 0 | Q7 | |
| 299. | Cl | Cl | C₂H₅ | 0 | Q8 | |
| 300. | Cl | Cl | C₂H₅ | 1 | Q1 | |
| 301. | Cl | Cl | C₂H₅ | 1 | Q3 | |
| 302. | Cl | Cl | C₂H₅ | 1 | Q4 | |
| 303. | Cl | Cl | C₂H₅ | 1 | Q5 | |
| 304. | Cl | Cl | C₂H₅ | 1 | Q6 | |
| 305. | Cl | Cl | C₂H₅ | 1 | Q7 | |
| 306. | Cl | Cl | C₃H₇-n | 0 | Q1 | |
| 307. | Cl | Cl | C₃H₇-n | 0 | Q6 | |
| 308. | Cl | Cl | C₃H₇-n | 1 | Q1 | |
| 309. | Cl | Cl | C₃H₇-n | 1 | Q6 | |
| 310. | Cl | Cl | C₃H₇-iso | 0 | Q1 | |
| 311. | Cl | Cl | C₃H₇-iso | 0 | Q6 | |
| 312. | Cl | Cl | C₃H₇-iso | 1 | Q1 | |
| 313. | Cl | Cl | C₃H₇-iso | 1 | Q6 | |
| 314. | Cl | Cl | cyclopropyl | 1 | Q1 | 1.5932 |
| 315. | Cl | Cl | cyclopropyl | 1 | Q2 | |
| 316. | Cl | Cl | cyclopropyl | 1 | Q4 | amorphous |
| 317. | Cl | Cl | 1-fluoro-2-methylcyclopropyl | 1 | Q6 | |
| 318. | Cl | Cl | 2-methylcyclopropyl | 1 | Q1 | |
| 319. | Cl | Cl | 2-fluorocyclopropyl | 1 | Q4 | |
| 320. | Cl | Cl | cyclopropyl | 1 | Q5 | |
| 321. | Cl | Cl | cyclopropyl | 1 | Q6 | 1.5510 |
| 322. | Cl | Cl | cyclopropyl | 1 | Q7 | 1.5929 |
| 323. | Cl | Cl | cyclopropyl | 1 | Q8 | amorphous |

TABLE 2-continued

[Structure: benzoate with Q-O-C(=O)- group, X substituent, (CH2)n linker to tetrazolinone N-R2, Z substituent on ring]

| Compound No. | X | Z | R² | n | Q | Property ($n_{20}^D$ or mp. °C.) |
|---|---|---|---|---|---|---|
| 324. | Cl | Cl | cyclohexyl-H | 1 | Q1 | |
| 325. | Cl | Cl | cyclohexyl-H | 1 | Q6 | |
| 326. | Cl | Cl | phenyl | 1 | Q1 | |
| 327. | Cl | Cl | phenyl | 1 | Q6 | |
| 328. | Cl | Cl | 2-Cl-phenyl | 1 | Q1 | |
| 329. | Cl | Cl | $CHF_2$ | 0 | Q1 | |
| 330. | Cl | Cl | $CHF_2$ | 0 | Q4 | |
| 331. | Cl | Cl | $CHF_2$ | 0 | Q6 | |
| 332. | Cl | Cl | $CHF_2$ | 0 | Q7 | |
| 333. | Cl | Cl | $CH_2CH_2CH_2F$ | 0 | Q1 | 1.5870 |
| 334. | Cl | Cl | $CH_2CH_2CH_2F$ | 0 | Q4 | |
| 335. | Cl | Cl | $CH_2CH_2CH_2F$ | 0 | Q6 | |
| 336. | Cl | Cl | $CH_2CH_2CH_2F$ | 0 | Q7 | |
| 337. | Cl | Cl | $CH_2CF_3$ | 1 | Q1 | |
| 338. | Cl | Cl | $CH_2CF_3$ | 1 | Q5 | |
| 339. | Cl | Cl | $CH_2CF_2CF_3$ | 1 | Q1 | |
| 340. | Cl | Cl | $CH_2CF_2CF_3$ | 1 | Q7 | |
| 341. | Cl | $OCH_3$ | $CH_3$ | 1 | Q1 | |
| 342. | Cl | $OCH_3$ | $CH_3$ | 1 | Q6 | |
| 343. | Cl | $OCH_3$ | $CH_3$ | 1 | Q7 | |
| 344. | Cl | $OCH_3$ | $C_2H_5$ | 1 | Q1 | |
| 345. | Cl | $OCH_3$ | cyclopropyl | 1 | Q1 | |
| 346. | Cl | $SCH_3$ | $CH_3$ | 1 | Q1 | |
| 347. | Cl | $SCH_3$ | $CH_3$ | 1 | Q6 | |
| 348. | Cl | $SCH_3$ | $CH_3$ | 1 | Q7 | |
| 349. | Cl | $SCH_3$ | $C_2H_5$ | 1 | Q1 | |
| 350. | Cl | $SCH_3$ | cyclopropyl | 1 | Q1 | |
| 351. | Cl | $SO_2CH_3$ | $CH_3$ | 0 | Q1 | |
| 352. | Cl | $SO_2CH_3$ | $CH_3$ | 0 | Q2 | |
| 353. | Cl | $SO_2CH_3$ | $CH_3$ | 0 | Q4 | |
| 354. | Cl | $SO_2CH_3$ | $CH_3$ | 0 | Q6 | |
| 355. | Cl | $SO_2CH_3$ | $CH_3$ | 0 | Q7 | |
| 356. | Cl | $SO_2CH_3$ | $CH_3$ | 0 | Q8 | |
| 357. | Cl | $SO_2CH_3$ | $CH_3$ | 1 | Q1 | |
| 358. | Cl | $SO_2CH_3$ | $CH_3$ | 1 | Q2 | |
| 359. | Cl | $SO_2CH_3$ | $CH_3$ | 1 | Q3 | |
| 360. | Cl | $SO_2CH_3$ | $CH_3$ | 1 | Q4 | |
| 361. | Cl | $SO_2CH_3$ | $CH_3$ | 1 | Q5 | |
| 362. | Cl | $SO_2CH_3$ | $CH_3$ | 1 | Q6 | |

TABLE 2-continued

| Compound No. | X | Z | R² | n | Q | Property (n₂₀ᴰ or mp. °C.) |
|---|---|---|---|---|---|---|
| 363. | Cl | SO₂CH₃ | CH₃ | 1 | Q7 | |
| 364. | Cl | SO₂CH₃ | CH₃ | 1 | Q8 | |
| 365. | Cl | SO₂CH₃ | C₂H₅ | 0 | Q1 | |
| 366. | Cl | SO₂CH₃ | C₂H₅ | 0 | Q4 | |
| 367. | Cl | SO₂CH₃ | C₂H₅ | 0 | Q6 | |
| 368. | Cl | SO₂CH₃ | C₂H₅ | 0 | Q7 | |
| 369. | Cl | SO₂CH₃ | C₂H₅ | 0 | Q8 | |
| 370. | Cl | SO₂CH₃ | C₂H₅ | 1 | Q1 | |
| 371. | Cl | SO₂CH₃ | C₂H₅ | 1 | Q3 | |
| 372. | Cl | SO₂CH₃ | C₂H₅ | 1 | Q4 | |
| 373. | Cl | SO₂CH₃ | C₂H₅ | 1 | Q5 | |
| 374. | Cl | SO₂CH₃ | C₂H₅ | 1 | Q6 | |
| 375. | Cl | SO₂CH₃ | C₂H₅ | 1 | Q7 | |
| 376. | Cl | SO₂CH₃ | C₃H₇-n | 0 | Q1 | |
| 377. | Cl | SO₂CH₃ | C₃H₇-n | 0 | Q6 | |
| 378. | Cl | SO₂CH₃ | C₃H₇-n | 1 | Q1 | |
| 379. | Cl | SO₂CH₃ | C₃H₇-n | 1 | Q6 | |
| 380. | Cl | SO₂CH₃ | C₃H₇-iso | 0 | Q1 | |
| 381. | Cl | SO₂CH₃ | C₃H₇-iso | 0 | Q6 | |
| 382. | Cl | SO₂CH₃ | C₃H₇-iso | 1 | Q1 | |
| 383. | Cl | SO₂CH₃ | C₃H₇-iso | 1 | Q6 | |
| 384. | Cl | SO₂CH₃ |  | 1 | Q1 | |
| 385. | Cl | SO₂CH₃ |  | 1 | Q2 | |
| 386. | Cl | SO₂CH₃ |  | 1 | Q4 | |
| 387. | Cl | SO₂CH₃ |  | 1 | Q5 | |
| 388. | Cl | SO₂CH₃ |  | 1 | Q6 | |
| 389. | Cl | SO₂CH₃ |  | 1 | Q7 | |
| 390. | Cl | SO₂CH₃ | 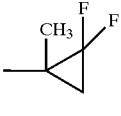 | 1 | Q8 | |
| 391. | Cl | SO₂CH₃ | 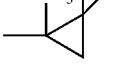 | 1 | Q4 | |
| 392. | Cl | SO₂CH₃ | 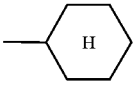 | 1 | Q5 | |
| 393. | Cl | SO₂CH₃ | 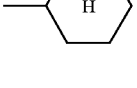 | 1 | Q1 | |
| 394. | Cl | SO₂CH₃ |  | 1 | Q6 | |

TABLE 2-continued

[Structure: benzene ring with Q-O-C(=O)- at one position, X at ortho, -(CH2)n- linked to a tetrazolinone ring N-R2, and Z at another position]

| Compound No. | X | Z | R² | n | Q | Property ($n_{20}^D$ or mp. °C.) |
|---|---|---|---|---|---|---|
| 395. | Cl | $SO_2CH_3$ | (phenyl) | 1 | Q1 | |
| 396. | Cl | $SO_2CH_3$ | (phenyl) | 1 | Q6 | |
| 397. | Cl | $SO_2CH_3$ | (2-Cl-phenyl) | 1 | Q1 | |
| 398. | Cl | $SO_2CH_3$ | $CHF_2$ | 0 | Q1 | |
| 399. | Cl | $SO_2CH_3$ | $CHF_2$ | 0 | Q4 | |
| 400. | Cl | $SO_2CH_3$ | $CHF_2$ | 0 | Q6 | |
| 401. | Cl | $SO_2CH_3$ | $CHF_2$ | 0 | Q7 | |
| 402. | Cl | $SO_2CH_3$ | $CH_2CH_2CH_2F$ | 0 | Q1 | |
| 403. | Cl | $SO_2CH_3$ | $CH_2CH_2CH_2F$ | 0 | Q4 | |
| 404. | Cl | $SO_2CH_3$ | $CH_2CH_2CH_2F$ | 0 | Q6 | |
| 405. | Cl | $SO_2CH_3$ | $CH_2CH_2CH_2F$ | 0 | Q7 | |
| 406. | Cl | $SO_2CH_3$ | $CH_2CF_3$ | 1 | Q1 | |
| 407. | Cl | $SO_2CH_3$ | $CH_2CF_3$ | 1 | Q7 | |
| 408. | Cl | $SO_2CH_3$ | $CH_2CF_2CF_3$ | 1 | Q1 | |
| 409. | Cl | $SO_2CH_3$ | $CH_2CF_2CF_3$ | 1 | Q6 | |
| 410. | $CH_3$ | $SO_2CH_3$ | $CH_3$ | 0 | Q1 | |
| 411. | $CH_3$ | $SO_2CH_3$ | $CH_3$ | 0 | Q6 | |
| 412. | $CH_3$ | $SO_2CH_3$ | $CH_3$ | 0 | Q7 | |
| 413. | $CH_3$ | $SO_2CH_3$ | $CH_3$ | 1 | Q1 | |
| 414. | $CH_3$ | $SO_2CH_3$ | $CH_3$ | 1 | Q3 | |
| 415. | $CH_3$ | $SO_2CH_3$ | $CH_3$ | 1 | Q4 | |
| 416. | $CH_3$ | $SO_2CH_3$ | $CH_3$ | 1 | Q5 | |
| 417. | $CH_3$ | $SO_2CH_3$ | $CH_3$ | 1 | Q6 | |
| 418. | $CH_3$ | $SO_2CH_3$ | $CH_3$ | 1 | Q7 | |
| 419. | $CH_3$ | $SO_2CH_3$ | $CH_3$ | 1 | Q8 | |
| 420. | $CH_3$ | $SO_2CH_3$ | $C_2H_5$ | 0 | Q1 | |
| 421. | $CH_3$ | $SO_2CH_3$ | $C_2H_5$ | 0 | Q4 | |
| 422. | $CH_3$ | $SO_2CH_3$ | $C_2H_5$ | 1 | Q1 | |
| 423. | $CH_3$ | $SO_2CH_3$ | $C_2H_5$ | 1 | Q3 | |
| 424. | $CH_3$ | $SO_2CH_3$ | $C_2H_5$ | 1 | Q4 | |
| 425. | $CH_3$ | $SO_2CH_3$ | $C_2H_5$ | 1 | Q5 | |
| 426. | $CH_3$ | $SO_2CH_3$ | $C_2H_5$ | 1 | Q6 | |
| 427. | $CH_3$ | $SO_2CH_3$ | $C_2H_5$ | 1 | Q7 | |
| 428. | $CH_3$ | $SO_2CH_3$ | $C_3H_7$-n | 0 | Q1 | |
| 429. | $CH_3$ | $SO_2CH_3$ | $C_3H_7$-n | 1 | Q1 | |
| 430. | $CH_3$ | $SO_2CH_3$ | $C_3H_7$-n | 1 | Q6 | |
| 431. | $CH_3$ | $SO_2CH_3$ | $C_3H_7$-iso | 0 | Q1 | |
| 432. | $CH_3$ | $SO_2CH_3$ | $C_3H_7$-iso | 1 | Q1 | |
| 433. | $CH_3$ | $SO_2CH_3$ | $C_3H_7$-iso | 1 | Q6 | |
| 434. | $CH_3$ | $SO_2CH_3$ | (cyclopropyl) | 1 | Q1 | |
| 435. | $CH_3$ | $SO_2CH_3$ | (cyclopropyl) | 1 | Q2 | |
| 436. | $CH_3$ | $SO_2CH_3$ | (cyclopropyl) | 1 | Q4 | |
| 437. | $CH_3$ | $SO_2CH_3$ | (cyclopropyl) | 1 | Q5 | |

TABLE 2-continued

| Compound No. | X | Z | R² | n | Q | Property ($n_{20}^D$ or mp. °C.) |
|---|---|---|---|---|---|---|
| 438. | CH₃ | SO₂CH₃ |  | 1 | Q6 | |
| 439. | CH₃ | SO₂CH₃ |  | 1 | Q7 | |
| 440. | CH₃ | SO₂CH₃ | 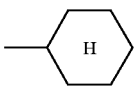 | 1 | Q8 | |
| 441. | CH₃ | SO₂CH₃ | 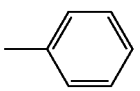 | 1 | Q1 | |
| 442. | CH₃ | SO₂CH₃ | 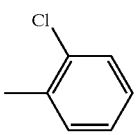 | 1 | Q1 | |
| 443. | CH₃ | SO₂CH₃ |  | 1 | Q1 | |
| 444. | CH₃ | SO₂CH₃ | CHF₂ | 0 | Q1 | |
| 445. | CH₃ | SO₂CH₃ | CH₂CH₂CH₂F | 0 | Q1 | |
| 446. | CH₃ | SO₂CH₃ | CH₂CF₃ | 1 | Q4 | |
| 447. | CH₃ | SO₂CH₃ | CH₂CF₂CF₃ | 1 | Q1 | |
| 448. | SCH₃ | Cl | CH₃ | 0 | Q1 | 66–73 |
| 449. | SCH₃ | Cl | CH₃ | 0 | Q2 | |
| 450. | SCH₃ | Cl | CH₃ | 0 | Q4 | |
| 451. | SCH₃ | Cl | CH₃ | 0 | Q5 | |
| 452. | SCH₃ | Cl | CH₃ | 0 | Q6 | 236–240 |
| 453. | SCH₃ | Cl | CH₃ | 0 | Q7 | |
| 454. | SCH₃ | Cl | CH₃ | 0 | Q8 | |
| 455. | SCH₃ | Cl | CH₃ | 1 | Q1 | 172–175 |
| 456. | SCH₃ | Cl | CH₃ | 1 | Q3 | |
| 457. | SCH₃ | Cl | CH₃ | 1 | Q4 | |
| 458. | SCH₃ | Cl | CH₃ | 1 | Q5 | |
| 459. | SCH₃ | Cl | CH₃ | 1 | Q6 | |
| 460. | SCH₃ | Cl | CH₃ | 1 | Q7 | |
| 461. | SCH₃ | Cl | CH₃ | 1 | Q8 | |
| 462. | SCH₃ | Cl | C₂H₅ | 0 | Q1 | |
| 463. | SCH₃ | Cl | C₂H₅ | 0 | Q4 | |
| 464. | SCH₃ | Cl | C₂H₅ | 0 | Q6 | |
| 465. | SCH₃ | Cl | C₂H₅ | 0 | Q7 | |
| 466. | SCH₃ | Cl | C₂H₅ | 0 | Q8 | |
| 467. | SCH₃ | Cl | C₂H₅ | 1 | Q1 | |
| 468. | SCH₃ | Cl | C₂H₅ | 1 | Q3 | |
| 469. | SCH₃ | Cl | C₂H₅ | 1 | Q4 | |
| 470. | SCH₃ | Cl | C₂H₅ | 1 | Q5 | |
| 471. | SCH₃ | Cl | C₂H₅ | 1 | Q6 | |
| 472. | SCH₃ | Cl | C₂H₅ | 1 | Q7 | |
| 473. | SCH₃ | Cl | C₃H₇-n | 0 | Q1 | |
| 474. | SCH₃ | Cl | C₃H₇-n | 0 | Q6 | |
| 475. | SCH₃ | Cl | C₃H₇-n | 1 | Q1 | |
| 476. | SCH₃ | Cl | C₃H₇-n | 1 | Q6 | |
| 477. | SCH₃ | Cl | C₃H₇-iso | 0 | Q1 | |
| 478. | SCH₃ | Cl | C₃H₇-iso | 0 | Q6 | |
| 479. | SCH₃ | Cl | C₃H₇-iso | 1 | Q1 | |
| 480. | SCH₃ | Cl | C₃H₇-iso | 1 | Q4 | |
| 481. | SCH₃ | Cl | C₃H₇-iso | 1 | Q6 | |

TABLE 2-continued

| Compound No. | X | Z | R² | n | Q | Property (n₂₀ᴰ or mp. °C.) |
|---|---|---|---|---|---|---|
| 482. | SCH₃ | Cl |  | 1 | Q1 | |
| 483. | SCH₃ | Cl |  | 1 | Q2 | |
| 484. | SCH₃ | Cl |  | 1 | Q4 | |
| 485. | SCH₃ | Cl |  | 1 | Q5 | |
| 486. | SCH₃ | Cl |  | 1 | Q6 | |
| 487. | SCH₃ | Cl |  | 1 | Q7 | |
| 488. | SCH₃ | Cl | 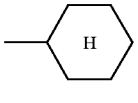 | 1 | Q8 | |
| 489. | SCH₃ | Cl | 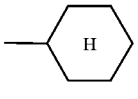 | 1 | Q1 | |
| 490. | SCH₃ | Cl | 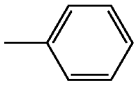 | 1 | Q6 | |
| 491. | SCH₃ | Cl | 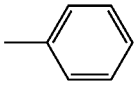 | 1 | Q1 | |
| 492. | SCH₃ | Cl | 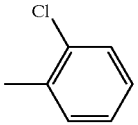 | 1 | Q6 | |
| 493. | SCH₃ | Cl |  | 1 | Q1 | |
| 494. | SCH₃ | Cl | CHF₂ | 0 | Q1 | |
| 495. | SCH₃ | Cl | CHF₂ | 0 | Q6 | |
| 496. | SCH₃ | Cl | CHF₂ | 0 | Q7 | |
| 497. | SCH₃ | Cl | CH₂CH₂CH₂F | 0 | Q1 | |
| 498. | SCH₃ | Cl | CH₂CH₂CH₂F | 0 | Q4 | |
| 499. | SCH₃ | Cl | CH₂CH₂CH₂F | 0 | Q6 | |
| 500. | SCH₃ | Cl | CH₂CH₂CH₂F | 0 | Q7 | |
| 501. | SCH₃ | Cl | CH₂CF₃ | 1 | Q1 | |
| 502. | SCH₃ | Cl | CH₂CF₂CF₃ | 1 | Q4 | |
| 503. | SCH₃ | SCH₃ | CH₃ | 0 | Q1 | |
| 504. | SCH₃ | SCH₃ | CH₃ | 0 | Q3 | |
| 5O5. | SCH₃ | SCH₃ | CH₃ | 0 | Q4 | |
| 506. | SCH₃ | SCH₃ | CH₃ | 0 | Q5 | |
| 507. | SCH₃ | SCH₃ | CH₃ | 0 | Q6 | |
| 508. | SCH₃ | SCH₃ | CH₃ | 0 | Q7 | |
| 509. | SCH₃ | SCH₃ | CH₃ | 0 | Q8 | |
| 510. | SCH₃ | SCH₃ | CH₃ | 1 | Q1 | 134–141 |

TABLE 2-continued

| Compound No. | X | Z | R² | n | Q | Property ($n_{20}^D$ or mp. °C.) |
|---|---|---|---|---|---|---|
| 511. | SCH₃ | SCH₃ | CH₃ | 1 | Q2 | |
| 512. | SCH₃ | SCH₃ | CH₃ | 1 | Q4 | |
| 513. | SCH₃ | SCH₃ | CH₃ | 1 | Q5 | |
| 514. | SCH₃ | SCH₃ | CH₃ | 1 | Q6 | |
| 515. | SCH₃ | SCH₃ | CH₃ | 1 | Q7 | |
| 516. | SCH₃ | SCH₃ | CH₃ | 1 | Q8 | |
| 517. | SCH₃ | SCH₃ | C₂H₅ | 0 | Q1 | |
| 518. | SCH₃ | SCH₃ | C₂H₅ | 0 | Q4 | |
| 519. | SCH₃ | SCH₃ | C₂H₅ | 0 | Q5 | |
| 520. | SCH₃ | SCH₃ | C₂H₅ | 0 | Q6 | |
| 521. | SCH₃ | SCH₃ | C₂H₅ | 0 | Q7 | |
| 522. | SCH₃ | SCH₃ | C₂H₅ | 1 | Q1 | |
| 523. | SCH₃ | SCH₃ | C₂H₅ | 1 | Q3 | |
| 524. | SCH₃ | SCH₃ | C₂H₅ | 1 | Q4 | |
| 525. | SCH₃ | SCH₃ | C₂H₅ | 1 | Q6 | |
| 526. | SCH₃ | SCH₃ | C₂H₅ | 1 | Q7 | |
| 527. | SCH₃ | SCH₃ | C₂H₅ | 1 | Q8 | |
| 528. | SCH₃ | SCH₃ | C₃H₇-n | 0 | Q1 | |
| 529. | SCH₃ | SCH₃ | C₃H₇-n | 0 | Q6 | |
| 530. | SCH₃ | SCH₃ | C₃H₇-n | 1 | Q1 | |
| 531. | SCH₃ | SCH₃ | C₃H₇-n | 1 | Q6 | |
| 532. | SCH₃ | SCH₃ | C₃H₇-iso | 0 | Q1 | |
| 533. | SCH₃ | SCH₃ | C₃H₇-iso | 0 | Q6 | |
| 534. | SCH₃ | SCH₃ | C₃H₇-iso | 1 | Q1 | |
| 535. | SCH₃ | SCH₃ | C₃H₇-iso | 1 | Q4 | |
| 536. | SCH₃ | SCH₃ | C₃H₇-iso | 1 | Q6 | |
| 537. | SCH₃ | SCH₃ |  | 1 | Q1 | |
| 538. | SCH₃ | SCH₃ |  | 1 | Q2 | |
| 539. | SCH₃ | SCH₃ |  | 1 | Q4 | |
| 540. | SCH₃ | SCH₃ |  | 1 | Q5 | |
| 541. | SCH₃ | SCH₃ |  | 1 | Q6 | |
| 542. | SCH₃ | SCH₃ |  | 1 | Q7 | |
| 543. | SCH₃ | SCH₃ | 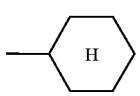 | 1 | Q8 | |
| 544. | SCH₃ | SCH₃ | 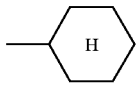 | 1 | Q1 | |
| 545. | SCH₃ | SCH₃ | 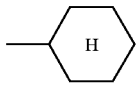 | 1 | Q6 | |
| 546. | SCH₃ | SCH₃ | 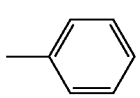 | 1 | Q1 | |

TABLE 2-continued

| Compound No. | X | Z | R² | n | Q | Property ($n_{20}^D$ or mp. °C.) |
|---|---|---|---|---|---|---|
| 547. | SCH₃ | SCH₃ | 2-Cl-C₆H₄ | 1 | Q1 | |
| 548. | SCH₃ | SCH₃ | CHF₂ | 0 | Q1 | |
| 549. | SCH₃ | SCH₃ | CH₂CH₂CH₂F | 0 | Q1 | |
| 550. | SCH₃ | SCH₃ | CH₂CF₃ | 1 | Q6 | |
| 551. | SCH₃ | SCH₃ | CH₂CF₂CF₃ | 1 | Q7 | |
| 552. | SO₂CH₃ | Cl | CH₃ | 0 | Q1 | amorphous |
| 553. | SO₂CH₃ | Cl | CH₃ | 0 | Q2 | |
| 554. | SO₂CH₃ | Cl | CH₃ | 0 | Q4 | |
| 555. | SO₂CH₃ | Cl | CH₃ | 0 | Q5 | |
| 556. | SO₂CH₃ | Cl | CH₃ | 0 | Q6 | 84–91 |
| 557. | SO₂CH₃ | Cl | CH₃ | 0 | Q7 | |
| 558. | SO₂CH₃ | Cl | CH₃ | 0 | Q8 | |
| 559. | SO₂CH₃ | Cl | CH₃ | 1 | Q1 | 135–137 |
| 560. | SO₂CH₃ | Cl | CH₃ | 1 | Q3 | |
| 561. | SO₂CH₃ | Cl | CH₃ | 1 | Q4 | |
| 562. | SO₂CH₃ | Cl | CH₃ | 1 | Q5 | |
| 563. | SO₂CH₃ | Cl | CH₃ | 1 | Q6 | 109–117 |
| 564. | SO₂CH₃ | Cl | CH₃ | 1 | Q7 | 81–83 |
| 565. | SO₂CH₃ | Cl | CH₃ | 1 | Q8 | |
| 566. | SO₂CH₃ | Cl | C₂H₅ | 0 | Q1 | |
| 567. | SO₂CH₃ | Cl | C₂H₅ | 0 | Q4 | |
| 568. | SO₂CH₃ | Cl | C₂H₅ | 0 | Q6 | |
| 569. | SO₂CH₃ | Cl | C₂H₅ | 0 | Q7 | |
| 570. | SO₂CH₃ | Cl | C₂H₅ | 0 | Q8 | |
| 571. | SO₂CH₃ | Cl | C₂H₅ | 1 | Q1 | |
| 572. | SO₂CH₃ | Cl | C₂H₅ | 1 | Q2 | |
| 573. | SO₂CH₃ | Cl | C₂H₅ | 1 | Q4 | |
| 574. | SO₂CH₃ | Cl | C₂H₅ | 1 | Q5 | |
| 575. | SO₂CH₃ | Cl | C₂H₅ | 1 | Q6 | |
| 576. | SO₂CH₃ | Cl | C₂H₅ | 1 | Q7 | |
| 577. | SO₂CH₃ | Cl | C₃H₇-n | 0 | Q1 | |
| 578. | SO₂CH₃ | Cl | C₃H₇-n | 0 | Q6 | |
| 579. | SO₂CH₃ | Cl | C₃H₇-n | 1 | Q1 | |
| 580. | SO₂CH₃ | Cl | C₃H₇-n | 1 | Q6 | |
| 581. | SO₂CH₃ | Cl | C₃H₇-iso | 0 | Q1 | |
| 582. | SO₂CH₃ | Cl | C₃H₇-iso | 0 | Q6 | |
| 583. | SO₂CH₃ | Cl | C₃H₇-iso | 1 | Q1 | |
| 584. | SO₂CH₃ | Cl | C₃H₇-iso | 1 | Q4 | |
| 585. | SO₂CH₃ | Cl | C₃H₇-iso | 1 | Q6 | |
| 586. | SO₂CH₃ | Cl | cyclopropyl | 1 | Q1 | |
| 587. | SO₂CH₃ | Cl | cyclopropyl | 1 | Q3 | |
| 588. | SO₂CH₃ | Cl | cyclopropyl | 1 | Q4 | |
| 589. | SO₂CH₃ | Cl | cyclopropyl | 1 | Q5 | |
| 590. | SO₂CH₃ | Cl | cyclopropyl | 1 | Q6 | |
| 591. | SO₂CH₃ | Cl | cyclopropyl | 1 | Q7 | |

TABLE 2-continued

| Compound No. | X | Z | R² | n | Q | Property (n₂₀D or mp. °C.) |
|---|---|---|---|---|---|---|
| 592. | SO₂CH₃ | Cl | 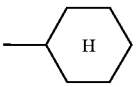 | 1 | Q8 | |
| 593. | SO₂CH₃ | Cl | 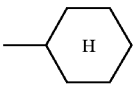 | 1 | Q1 | |
| 594. | SO₂CH₃ | Cl | 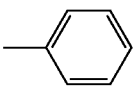 | 1 | Q6 | |
| 595. | SO₂CH₃ | Cl | 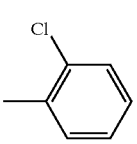 | 1 | Q1 | |
| 596. | SO₂CH₃ | Cl |  | 1 | Q1 | |
| 597. | SO₂CH₃ | Cl | CHF₂ | 0 | Q1 | |
| 598. | SO₂CH₃ | Cl | CH₂CH₂CH₂F | 0 | Q1 | |
| 599. | SO₂CH₃ | Cl | CH₂CF₃ | 1 | Q1 | |
| 600. | SO₂CH₃ | Cl | CH₂CF₂CF₃ | 1 | Q1 | |
| 601. | SO₂CH₃ | SO₂CH₃ | CH₃ | 0 | Q1 | |
| 602. | SO₂CH₃ | SO₂CH₃ | CH₃ | 0 | Q3 | |
| 603. | SO₂CH₃ | SO₂CH₃ | CH₃ | 0 | Q4 | |
| 604. | SO₂CH₃ | SO₂CH₃ | CH₃ | 0 | Q5 | |
| 605. | SO₂CH₃ | SO₂CH₃ | CH₃ | 0 | Q6 | |
| 606. | SO₂CH₃ | SO₂CH₃ | CH₃ | 0 | Q7 | |
| 607. | SO₂CH₃ | SO₂CH₃ | CH₃ | 0 | Q8 | |
| 608. | SO₂CH₃ | SO₂CH₃ | CH₃ | 1 | Q1 | |
| 609. | SO₂CH₃ | SO₂CH₃ | CH₃ | 1 | Q2 | |
| 610. | SO₂CH₃ | SO₂CH₃ | CH₃ | 1 | Q4 | |
| 611. | SO₂CH₃ | SO₂CH₃ | CH₃ | 1 | Q5 | |
| 612. | SO₂CH₃ | SO₂CH₃ | CH₃ | 1 | Q6 | |
| 613. | SO₂CH₃ | SO₂CH₃ | CH₃ | 1 | Q7 | |
| 614. | SO₂CH₃ | SO₂CH₃ | CH₃ | 1 | Q8 | |
| 615. | SO₂CH₃ | SO₂CH₃ | C₂H₅ | 0 | Q1 | |
| 616. | SO₂CH₃ | SO₂CH₃ | C₂H₅ | 0 | Q4 | |
| 617. | SO₂CH₃ | SO₂CH₃ | C₂H₅ | 0 | Q6 | |
| 618. | SO₂CH₃ | SO₂CH₃ | C₂H₅ | 0 | Q7 | |
| 619. | SO₂CH₃ | SO₂CH₃ | C₂H₅ | 1 | Q1 | |
| 620. | SO₂CH₃ | SO₂CH₃ | C₂H₅ | 1 | Q3 | |
| 621. | SO₂CH₃ | SO₂CH₃ | C₂H₅ | 1 | Q6 | |
| 622. | SO₂CH₃ | SO₂CH₃ | C₂H₅ | 1 | Q7 | |
| 623. | SO₂CH₃ | SO₂CH₃ | C₂H₅ | 1 | Q8 | |
| 624. | SO₂CH₃ | SO₂CH₃ | C₃H₇-n | 0 | Q1 | |
| 625. | SO₂CH₃ | SO₂CH₃ | C₃H₇-n | 0 | Q6 | |
| 626. | SO₂CH₃ | SO₂CH₃ | C₃H₇-n | 1 | Q1 | |
| 627. | SO₂CH₃ | SO₂CH₃ | C₃H₇-n | 1 | Q6 | |
| 628. | SO₂CH₃ | SO₂CH₃ | C₃H₇-iso | 0 | Q1 | |
| 629. | SO₂CH₃ | SO₂CH₃ | C₃H₇-iso | 0 | Q6 | |
| 630. | SO₂CH₃ | SO₂CH₃ | C₃H₇-iso | 1 | Q1 | |
| 631. | SO₂CH₃ | SO₂CH₃ | C₃H₇-iso | 1 | Q4 | |
| 632. | SO₂CH₃ | SO₂CH₃ | C₃H₇-iso | 1 | Q6 | |
| 633. | SO₂CH₃ | SO₂CH₃ | | 1 | Q1 | |

TABLE 2-continued

| Compound No. | X | Z | R² | n | Q | Property (n₂₀ᴅ or mp. °C.) |
|---|---|---|---|---|---|---|
| 634. | SO₂CH₃ | SO₂CH₃ | cyclopropyl | 1 | Q2 | |
| 635. | SO₂CH₃ | SO₂CH₃ | cyclopropyl | 1 | Q4 | |
| 636. | SO₂CH₃ | SO₂CH₃ | cyclopropyl | 1 | Q5 | |
| 637. | SO₂CH₃ | SO₂CH₃ | cyclopropyl | 1 | Q6 | |
| 638. | SO₂CH₃ | SO₂CH₃ | cyclopropyl | 1 | Q7 | |
| 639. | SO₂CH₃ | SO₂CH₃ | cyclopropyl | 1 | Q8 | |
| 640. | SO₂CH₃ | SO₂CH₃ | cyclohexyl | 1 | Q1 | |
| 641. | SO₂CH₃ | SO₂CH₃ | cyclohexyl | 1 | Q6 | |
| 642. | SO₂CH₃ | SO₂CH₃ | phenyl | 1 | Q1 | |
| 643. | SO₂CH₃ | SO₂CH₃ | 2-Cl-phenyl | 1 | Q1 | |
| 644. | SO₂CH₃ | SO₂CH₃ | CHF₂ | 0 | Q1 | |
| 645. | SO₂CH₃ | SO₂CH₃ | CH₂CH₂CH₂F | 0 | Q1 | |
| 646. | Cl | Cl | C₄H₉-n | 0 | Q1 | |
| 647. | Cl | Cl | C₄H₉-tet | 1 | Q1 | |
| 648. | Cl | Cl | C₄H₉-tert | 1 | Q6 | |
| 649. | Cl | Cl | C₅H₁₁-n | 0 | Q5 | |
| 650. | Cl | Cl | C₅H₁₁-n | 1 | Q6 | |
| 651. | Cl | Cl | 3-NO₂-phenyl | 1 | Q1 | |
| 652. | Cl | Cl | 4-Br-phenyl | 1 | Q1 | |

TABLE 2-continued

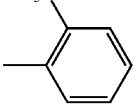

| Compound No. | X | Z | R² | n | Q | Property ($n_{20}^D$ or mp. °C.) |
|---|---|---|---|---|---|---|
| 653. | Cl | Cl | (2-methylphenyl) | 1 | Q5 | |
| 654. | Cl | Cl | (3-trifluoromethylphenyl) | 1 | Q6 | |
| 655. | Cl | Cl | (3-fluorophenyl) | 1 | Q6 | |
| 656. | Cl | Cl | CH₃ | 1 | Q9 | |
| 657. | Cl | Cl | CH₃ | 1 | Q10 | |
| 658. | Cl | Cl | CH₃ | 1 | Q11 | |
| 659. | Cl | SO₂CH₃ | $C_5H_{11}$-n | 1 | Q1 | |
| 660. | Cl | SO₂CH₃ | $C_4H_9$-tert | 1 | Q1 | |
| 661. | Cl | SO₂CH₃ | $C_4H_9$-tert | 1 | Q6 | |
| 662. | Cl | SO₂CH₃ | (2-ethylphenyl) CH₂—CH₃ | 1 | Q1 | |
| 663. | Cl | SO₂CH₃ | (3-difluoromethylphenyl) CHF₂ | 1 | Q1 | |
| 664. | Cl | SO₂CH₃ | (4-fluorophenyl) | 1 | Q5 | |
| 665. | Cl | SO₂CH₃ | (4-methylphenyl) | 1 | Q6 | |
| 666. | Cl | SO₂CH₃ | (2-ethylphenyl) CH₂—CH₃ | 1 | Q1 | |
| 667. | Cl | SO₂CH₃ | CH₃ | 1 | Q9 | |
| 668. | Cl | SO₂CH₃ | CH₃ | 1 | Q10 | |
| 669. | Cl | SO₂CH₃ | CH₃ | 1 | Q11 | |
| 670. | Cl | SO₂C₂H₅ | CH₃ | 1 | Q1 | |
| 671. | Cl | SO₂C₂H₅ | CH₃ | 1 | Q6 | |
| 672. | Cl | SO₂C₃H₇-n | CH₃ | 1 | Q1 | |
| 673. | SC₂H₅ | Cl | CH₃ | 0 | Q1 | |
| 674. | SC₂H₅ | Cl | CH₃ | 0 | Q6 | |
| 675. | SC₂H₅ | Cl | CH₃ | 1 | Q1 | |

TABLE 2-continued

| Compound No. | X | Z | R² | n | Q | Property ($n_{20}^D$ or mp. °C.) |
|---|---|---|---|---|---|---|
| 676. | SC₃H₇-n | Cl | CH₃ | 0 | Q1 | |
| 677. | SO₂C₂H₅ | Cl | CH₃ | 0 | Q1 | |
| 678. | SO₂C₃H₇-n | Cl | CH₃ | 1 | Q1 | |
| 678a | Br | Br | CH₃ | 1 | Q1 | 67–68 |
| 678b | Br | Br | C₂H₅ | 1 | Q1 | |
| 678c | Br | Br |  | 1 | Q1 | |
| 678d | Br | SO₂CH₃ | CH₃ | 1 | Q1 | 96–102 |
| 678e | Br | SO₂CH₃ | CH₃ | 1 | Q4 | |
| 678f | Br | SO₂CH₃ | C₂H₅ | 1 | Q1 | |
| 678g | Br | SO₂CH₃ |  | 1 | Q1 | 134–135 |
| 678h | Br | SO₂CH₃ |  | 1 | Q4 | |
| 678i | OCH₃ | Cl | CH₃ | 1 | Q1 | |
| 678j | OCH₃ | Cl | C₂H₅ | 1 | Q1 | |
| 678k | OCH₃ | Cl | (cyclopropyl) | 1 | Q1 | |

TABLE 3

| Compound No. | X | Y | R² | n | Q | Property ($n_{20}^D$ or mp. °C.) |
|---|---|---|---|---|---|---|
| 679. | H | H | CH₃ | 0 | Q1 | |
| 680. | H | H | CH₃ | 0 | Q4 | |
| 681. | H | H | CH₃ | 0 | Q6 | |
| 682. | H | H | CH₃ | 1 | Q1 | |
| 683. | H | H | CH₃ | 1 | Q5 | |
| 684. | H | H | CH₃ | 1 | Q7 | |
| 685. | H | CH₃ | CH₃ | 0 | Q1 | |
| 686. | H | CH₃ | CH₃ | 0 | Q6 | |
| 687. | H | OCH₃ | CH₃ | 0 | Q1 | 54–59 |
| 688. | H | OCH₃ | CH₃ | 1 | Q1 | |
| 689. | H | NO₂ | CH₃ | 0 | Q1 | |
| 690. | H | NO₂ | CH₃ | 1 | Q1 | |
| 691. | F | H | CH₃ | 0 | Q1 | |
| 692. | F | H | CH₃ | 0 | Q4 | |
| 693. | F | H | CH₃ | 0 | Q6 | |
| 694. | F | H | CH₃ | 1 | Q1 | |
| 695. | F | H | CH₃ | 1 | Q5 | |
| 696. | F | H | CH₃ | 1 | Q7 | |
| 697. | F | H | C₂H₅ | 0 | Q1 | |
| 698. | F | H | C₃H₇-n | 1 | Q1 | |
| 699. | F | H | C₃H₇-iso | 0 | Q1 | |
| 700. | F | H | C₃H₇-iso | 1 | Q1 | |

TABLE 3-continued

| Compound No. | X | Y | R² | n | Q | Property ($n_{20}^D$ or mp. °C.) |
|---|---|---|---|---|---|---|
| 701. | F | H | cyclopropyl | 1 | Q1 | |
| 702. | F | H | cyclopropyl | 1 | Q6 | |
| 703. | F | H | phenyl | 1 | Q1 | |
| 704. | F | H | CHF₂ | 0 | Q1 | |
| 705. | Cl | H | CH₃ | 0 | Q1 | 178–179 |
| 706. | Cl | H | CH₃ | 0 | Q4 | |
| 707. | Cl | H | CH₃ | 0 | Q5 | |
| 708. | Cl | H | CH₃ | 0 | Q6 | |
| 709. | Cl | H | CH₃ | 0 | Q7 | 154–157 |
| 710. | Cl | H | CH₃ | 0 | Q8 | 174–176 |
| 711. | Cl | H | CH₃ | 1 | Q1 | |
| 712. | Cl | H | CH₃ | 1 | Q2 | |
| 713. | Cl | H | CH₃ | 1 | Q4 | |
| 714. | Cl | H | CH₃ | 1 | Q6 | |
| 715. | Cl | H | CH₃ | 1 | Q8 | |
| 716. | Cl | H | C₂H₅ | 0 | Q1 | |
| 711. | Cl | H | C₂H₅ | 0 | Q2 | |
| 718. | Cl | H | C₂H₅ | 0 | Q4 | |
| 719. | Cl | H | C₂H₅ | 0 | Q6 | |
| 720. | Cl | H | C₂H₅ | 0 | Q7 | |
| 721. | Cl | H | C₂H₅ | 1 | Q1 | |
| 722. | Cl | H | C₂H₅ | 1 | Q7 | |
| 723. | Cl | H | C₃H₇-n | 0 | Q1 | |
| 724. | Cl | H | C₃H₇-n | 0 | Q6 | |
| 725. | Cl | H | C₃H₇-n | 1 | Q1 | |
| 726. | Cl | H | C₃H₇-n | 1 | Q6 | |
| 727. | Cl | H | C₃H₇-iso | 0 | Q1 | |
| 728. | Cl | H | C₃H₇-iso | 0 | Q7 | |
| 729. | Cl | H | C₃H₇-iso | 1 | Q1 | |
| 730. | Cl | H | cyclopropyl | 1 | Q1 | |
| 731. | Cl | H | cyclopropyl | 1 | Q6 | |
| 732. | Cl | H | cyclopropyl | 1 | Q8 | |
| 733. | Cl | H | cyclohexyl | 1 | Q1 | |
| 734. | Cl | H | cyclohexyl | 1 | Q4 | |
| 735. | Cl | H | phenyl | 1 | Q1 | |

TABLE 3-continued

| Compound No. | X | Y | R² | n | Q | Property (n₂₀ᴰ or mp. °C.) |
|---|---|---|---|---|---|---|
| 736. | Cl | H | 2-Cl-phenyl | 1 | Q1 | |
| 737. | Cl | H | CHF₂ | 0 | Q1 | |
| 738. | Cl | H | CHF₂ | 0 | Q5 | |
| 739. | Cl | H | CH₂CH₂CH₂F | 0 | Q1 | |
| 740. | Cl | H | CH₂CF₃ | 1 | Q1 | |
| 741. | Br | H | CH₃ | 0 | Q1 | |
| 742. | Br | H | CH₃ | 0 | Q2 | |
| 743. | Br | H | CH₃ | 0 | Q4 | |
| 744. | Br | H | CH₃ | 0 | Q5 | |
| 745. | Br | H | CH₃ | 0 | Q6 | |
| 746. | Br | H | CH₃ | 0 | Q7 | |
| 747. | Br | H | CH₃ | 0 | Q8 | |
| 748. | Br | H | CH₃ | 1 | Q1 | |
| 749. | Br | H | CH₃ | 1 | Q4 | |
| 750. | Br | H | CH₃ | 1 | Q6 | |
| 751. | Br | H | CH₃ | 1 | Q8 | |
| 752. | Br | H | C₂H₅ | 0 | Q1 | |
| 753. | Br | H | C₂H₅ | 0 | Q3 | |
| 754. | Br | H | C₂H₅ | 0 | Q4 | |
| 755. | Br | H | C₂H₅ | 0 | Q5 | |
| 756. | Br | H | C₂H₅ | 0 | Q8 | |
| 757. | Br | H | C₂H₅ | 1 | Q1 | |
| 758. | Br | H | C₂H₅ | 1 | Q6 | |
| 759. | Br | H | C₃H₇-n | 0 | Q1 | |
| 760. | Br | H | C₃H₇-n | 0 | Q6 | |
| 761. | Br | H | C₃H₇-n | 1 | Q1 | |
| 762. | Br | H | C₃H₇-n | 1 | Q6 | |
| 763. | Br | H | C₃H₇-iso | 0 | Q1 | |
| 764. | Br | H | C₃H₇-iso | 0 | Q6 | |
| 765. | Br | H | C₃H₇-iso | 1 | Q1 | |
| 766. | Br | H | cyclopropyl | 1 | Q1 | |
| 767. | Br | H | cyclopropyl | 1 | Q6 | |
| 768. | Br | H | cyclopropyl | 1 | Q8 | |
| 769. | Br | H | cyclohexyl-H | 1 | Q1 | |
| 770. | Br | H | phenyl | 1 | Q1 | |
| 771. | Br | H | 2-Cl-phenyl | 1 | Q1 | |
| 772. | Br | H | CHF₂ | 0 | Q1 | |

TABLE 3-continued

| Compound No. | X | Y | R² | n | Q | Property (n₂₀ᴅ or mp. °C.) |
|---|---|---|---|---|---|---|
| 773. | Br | H | CHF₂ | 0 | Q6 | |
| 774. | Br | H | CH₂CH₂CH₂F | 0 | Q1 | |
| 775. | Br | H | CH₂CF₂CF₃ | 1 | Q1 | |
| 776. | I | H | CH₃ | 0 | Q1 | |
| 777. | I | H | CH₃ | 0 | Q6 | |
| 778. | I | H | CH₃ | 0 | Q7 | |
| 779. | I | H | CH₃ | 1 | Q1 | |
| 780. | I | H | C₂H₅ | 0 | Q1 | |
| 781. | I | H | cyclopropyl | 1 | Q1 | |
| 782. | CH₃ | H | CH₃ | 0 | Q1 | |
| 783. | CH₃ | H | CH₃ | 0 | Q6 | |
| 784. | CH₃ | H | C₂H₅ | 0 | Q1 | |
| 785. | OCH₃ | H | CH₃ | 0 | Q1 | |
| 786. | OCH₃ | H | CH₃ | 0 | Q2 | |
| 787. | OCH₃ | H | CH₃ | 0 | Q4 | |
| 788. | OCH₃ | H | CH₃ | 0 | Q5 | |
| 789. | OCH₃ | H | CH₃ | 0 | Q6 | |
| 790. | OCH₃ | H | CH₃ | 0 | Q7 | |
| 791. | OCH₃ | H | CH₃ | 0 | Q8 | |
| 792. | OCH₃ | H | CH₃ | 1 | Q1 | |
| 793. | OCH₃ | H | CH₃ | 1 | Q4 | |
| 794. | OCH₃ | H | CH₃ | 1 | Q5 | |
| 795. | OCH₃ | H | CH₃ | 1 | Q6 | |
| 796. | OCH₃ | H | CH₃ | 1 | Q7 | |
| 797. | OCH₃ | H | C₂H₅ | 0 | Q1 | |
| 798. | OCH₃ | H | C₂H₅ | 0 | Q3 | |
| 799. | OCH₃ | H | C₂H₅ | 0 | Q4 | |
| 800. | OCH₃ | H | C₂H₅ | 0 | Q6 | |
| 801. | OCH₃ | H | C₂H₅ | 0 | Q7 | |
| 802. | OCH₃ | H | C₂H₅ | 1 | Q1 | |
| 803. | OCH₃ | H | C₂H₅ | 1 | Q5 | |
| 804. | OCH₃ | H | C₂H₅ | 1 | Q7 | |
| 805. | OCH₃ | H | C₃H₇-n | 0 | Q1 | |
| 806. | OCH₃ | H | C₃H₇-n | 0 | Q6 | |
| 807. | OCH₃ | H | C₃H₇-n | 1 | Q1 | |
| 808. | OCH₃ | H | C₃H₇-n | 1 | Q6 | |
| 809. | OCH₃ | H | C₃H₇-iso | 0 | Q1 | |
| 810. | OCH₃ | H | C₃H₇-iso | 0 | Q6 | |
| 811. | OCH₃ | H | C₃H₇-iso | 1 | Q1 | |
| 812. | OCH₃ | H | cyclopropyl | 1 | Q1 | |
| 813. | OCH₃ | H | cyclopropyl | 1 | Q6 | |
| 814. | OCH₃ | H | cyclopropyl | 1 | Q7 | |
| 815. | OCH₃ | H | cyclohexyl | 1 | Q1 | |
| 816. | OCH₃ | H | phenyl | 1 | Q1 | |

TABLE 3-continued

| Compound No. | X | Y | R² | n | Q | Property (n₂₀ᴰ or mp. °C.) |
|---|---|---|---|---|---|---|
| 817. | OCH₃ | H | 2-Cl-phenyl | 1 | Q1 | 1.5964 |
| 818. | OCH₃ | H | CHF₂ | 0 | Q1 | |
| 819. | OCH₃ | H | CHF₂ | 0 | Q6 | |
| 820. | OCH₃ | H | CH₂CH₂CH₂F | 0 | Q1 | |
| 821. | OCH₃ | H | CH₂CF₃ | 1 | Q1 | |
| 822. | OSO₂CH₃ | H | CH₃ | 0 | Q1 | |
| 823. | OSO₂CH₃ | H | CH₃ | 0 | Q3 | |
| 824. | OSO₂CH₃ | H | CH₃ | 0 | Q4 | |
| 825. | OSO₂CH₃ | H | CH₃ | 0 | Q5 | |
| 826. | OSO₂CH₃ | H | CH₃ | 0 | Q6 | |
| 827. | OSO₂CH₃ | H | CH₃ | 0 | Q7 | |
| 828. | OSO₂CH₃ | H | CH₃ | 0 | Q8 | |
| 829. | OSO₂CH₃ | H | CH₃ | 1 | Q1 | |
| 830. | OSO₂CH₃ | H | CH₃ | 1 | Q4 | |
| 831. | OSO₂CH₃ | H | CH₃ | 1 | Q5 | |
| 832. | OSO₂CH₃ | H | CH₃ | 1 | Q6 | |
| 833. | OSO₂CH₃ | H | CH₃ | 1 | Q7 | |
| 834. | OSO₂CH₃ | H | CH₃ | 1 | Q8 | |
| 835. | OSO₂CH₃ | H | C₂H₅ | 0 | Q1 | |
| 836. | OSO₂CH₃ | H | C₂H₅ | 0 | Q4 | |
| 837. | OSO₂CH₃ | H | C₂H₅ | 0 | Q5 | |
| 838. | OSO₂CH₃ | H | C₂H₅ | 0 | Q6 | |
| 839. | OSO₂CH₃ | H | C₂H₅ | 0 | Q7 | |
| 840. | OSO₂CH₃ | H | C₂H₅ | 1 | Q1 | |
| 841. | OSO₂CH₃ | H | C₂H₅ | 1 | Q6 | |
| 842. | OSO₂CH₃ | H | C₂H₅ | 1 | Q7 | |
| 843. | OSO₂CH₃ | H | C₃H₇-n | 0 | Q1 | |
| 844. | OSO₂CH₃ | H | C₃H₇-n | 0 | Q6 | |
| 845. | OSO₂CH₃ | H | C₃H₇-n | 1 | Q1 | |
| 846. | OSO₂CH₃ | H | C₃H₇-n | 1 | Q6 | |
| 847. | OSO₂CH₃ | H | C₃H₇-iso | 0 | Q1 | |
| 848. | OSO₂CH₃ | H | C₃H₇-iso | 0 | Q6 | |
| 849. | OSO₂CH₃ | H | C₃H₇-iso | 1 | Q1 | |
| 850. | OSO₂CH₃ | H | cyclopropyl | 1 | Q1 | |
| 851. | OSO₂CH₃ | H | cyclopropyl | 1 | Q6 | |
| 852. | OSO₂CH₃ | H | cyclopropyl | 1 | Q7 | |
| 853. | OSO₂CH₃ | H | cyclohexyl | 1 | Q1 | |
| 854. | OSO₂CH₃ | H | phenyl | 1 | Q1 | |

TABLE 3-continued

| Compound No. | X | Y | R² | n | Q | Property (n₂₀ᴅ or mp. °C.) |
|---|---|---|---|---|---|---|
| 855. | OSO₂CH₃ | H | 2-Cl-phenyl | 1 | Q1 | |
| 856. | OSO₂CH₃ | H | CHF₂ | 0 | Q1 | |
| 857. | OSO₂CH₃ | H | CHF₂ | 0 | Q4 | |
| 858. | OSO₂CH₃ | H | CH₂CH₂CH₂F | 0 | Q1 | |
| 859. | OSO₂CH₃ | H | CH₂CF₂CF₃ | 1 | Q1 | |
| 860. | SCH₃ | H | CH₃ | 0 | Q1 | |
| 861. | SCH₃ | H | CH₃ | 0 | Q2 | |
| 862. | SCH₃ | H | CH₃ | 0 | Q4 | |
| 863. | SCH₃ | H | CH₃ | 0 | Q5 | |
| 864. | SCH₃ | H | CH₃ | 0 | Q6 | |
| 865. | SCH₃ | H | CH₃ | 0 | Q7 | |
| 866. | SCH₃ | H | CH₃ | 0 | Q8 | |
| 867. | SCH₃ | H | CH₃ | 1 | Q1 | |
| 868. | SCH₃ | H | CH₃ | 1 | Q4 | |
| 869. | SCH₃ | H | CH₃ | 1 | Q5 | |
| 870. | SCH₃ | H | CH₃ | 1 | Q6 | |
| 871. | SCH₃ | H | CH₃ | 1 | Q7 | |
| 872. | SCH₃ | H | C₂H₅ | 0 | Q1 | |
| 873. | SCH₃ | H | C₂H₅ | 0 | Q6 | |
| 874. | SCH₃ | H | C₂H₅ | 0 | Q7 | |
| 875. | SCH₃ | H | C₂H₅ | 1 | Q1 | |
| 876. | SCH₃ | H | C₂H₅ | 1 | Q5 | |
| 877. | SCH₃ | H | C₂H₅ | 1 | Q7 | |
| 878. | SCH₃ | H | C₃H₇-n | 0 | Q1 | |
| 879. | SCH₃ | H | C₃H₇-n | 0 | Q6 | |
| 880. | SCH₃ | H | C₃H₇-n | 1 | Q1 | |
| 881. | SCH₃ | H | C₃H₇-iso | 0 | Q1 | |
| 882. | SCH₃ | H | C₃H₇-iso | 1 | Q1 | |
| 883. | SCH₃ | H | cyclopropyl | 1 | Q1 | |
| 884. | SCH₃ | H | cyclopropyl | 1 | Q6 | |
| 885. | SCH₃ | H | 2-Cl-phenyl | 1 | Q1 | |
| 886. | SCH₃ | H | CHF₂ | 0 | Q6 | |
| 887. | SCH₃ | H | CH₂CH₂CH₂F | 0 | Q1 | |
| 888. | SO₂CH₃ | H | CH₃ | 0 | Q1 | |
| 889. | SO₂CH₃ | H | CH₃ | 0 | Q2 | |
| 890. | SO₂CH₃ | H | CH₃ | 0 | Q4 | |
| 891. | SO₂CH₃ | H | CH₃ | 0 | Q5 | |
| 892. | SO₂CH₃ | H | CH₃ | 0 | Q6 | |
| 893. | SO₂CH₃ | H | CH₃ | 0 | Q7 | |
| 894. | SO₂CH₃ | H | CH₃ | 0 | Q8 | |
| 895. | SO₂CH₃ | H | CH₃ | 1 | Q1 | |
| 896. | SO₂CH₃ | H | CH₃ | 1 | Q4 | |
| 897. | SO₂CH₃ | H | CH₃ | 1 | Q5 | |
| 898. | SO₂CH₃ | H | CH₃ | 1 | Q6 | |
| 899. | SO₂CH₃ | H | CH₃ | 1 | Q7 | |
| 900. | SO₂CH₃ | H | CH₃ | 1 | Q8 | |
| 901. | SO₂CH₃ | H | C₂H₅ | 0 | Q1 | |

TABLE 3-continued

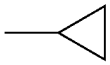

| Compound No. | X | Y | R² | n | Q | Property ($n_{20}^D$ or mp. ° C.) |
|---|---|---|---|---|---|---|
| 902. | SO₂CH₃ | H | C₂H₅ | 0 | Q6 | |
| 903. | SO₂CH₃ | H | C₂H₅ | 0 | Q7 | |
| 904. | SO₂CH₃ | H | C₂H₅ | 1 | Q1 | |
| 905. | SO₂CH₃ | H | C₂H₅ | 1 | Q5 | |
| 906. | SO₂CH₃ | H | C₂H₅ | 1 | Q7 | |
| 907. | SO₂CH₃ | H | C₃H₇-n | 0 | Q1 | |
| 908. | SO₂CH₃ | H | C₃H₇-n | 0 | Q6 | |
| 909. | SO₂CH₃ | H | C₃H₇-n | 1 | Q1 | |
| 910. | SO₂CH₃ | H | C₃H₇-iso | 0 | Q1 | |
| 911. | SO₂CH₃ | H | C₃H₇-iso | 0 | Q6 | |
| 912. | SO₂CH₃ | H | C₃H₇-iso | 1 | Q1 | |
| 913. | SO₂CH₃ | H | 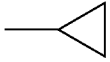 | 1 | Q1 | |
| 914. | SO₂CH₃ | H | 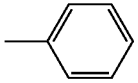 | 1 | Q6 | |
| 915. | SO₂CH₃ | H | 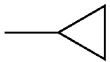 | 1 | Q1 | |
| 916. | SO₂CH₃ | H | CHF₂ | 0 | Q1 | |
| 917. | SO₂CH₃ | H | CH₂CH₂CH₂F | 0 | Q6 | |
| 918. | NO₂ | H | CH₃ | 0 | Q1 | |
| 919. | NO₂ | H | CH₃ | 0 | Q2 | |
| 920. | NO₂ | H | CH₃ | 0 | Q3 | |
| 921. | NO₂ | H | CH₃ | 0 | Q4 | |
| 922. | NO₂ | H | CH₃ | 0 | Q5 | |
| 923. | NO₂ | H | CH₃ | 0 | Q6 | |
| 924. | NO₂ | H | CH₃ | 0 | Q7 | |
| 925. | NO₂ | H | CH₃ | 0 | Q8 | |
| 926. | NO₂ | H | CH₃ | 1 | Q1 | |
| 927. | NO₂ | H | CH₃ | 1 | Q2 | |
| 928. | NO₂ | H | CH₃ | 1 | Q3 | |
| 929. | NO₂ | H | CH₃ | 1 | Q4 | |
| 930. | NO₂ | H | CH₃ | 1 | Q6 | |
| 931. | NO₂ | H | CH₃ | 1 | Q8 | |
| 932. | NO₂ | H | C₂H₅ | 0 | Q1 | |
| 933. | NO₂ | H | C₂H₅ | 0 | Q2 | |
| 934. | NO₂ | H | C₂H₅ | 0 | Q4 | |
| 935. | NO₂ | H | C₂H₅ | 0 | Q6 | |
| 936. | NO₂ | H | C₂H₅ | 0 | Q7 | |
| 937. | NO₂ | H | C₂H₅ | 1 | Q1 | |
| 938. | NO₂ | H | C₂H₅ | 1 | Q4 | |
| 939. | NO₂ | H | C₂H₅ | 1 | Q6 | |
| 940. | NO₂ | H | C₂H₅ | 1 | Q7 | |
| 941. | NO₂ | H | C₃H₇-n | 0 | Q1 | |
| 942. | NO₂ | H | C₃H₇-n | 0 | Q6 | |
| 943. | NO₂ | H | C₃H₇-n | 0 | Q7 | |
| 944. | NO₂ | H | C₃H₇-n | 1 | Q1 | |
| 945. | NO₂ | H | C₃H₇-n | 1 | Q6 | |
| 946. | NO₂ | H | C₃H₇-iso | 0 | Q1 | |
| 947. | NO₂ | H | C₃H₇-iso | 0 | Q6 | |
| 948. | NO₂ | H | C₃H₇-iso | 0 | Q7 | |
| 949. | NO₂ | H | C₃H₇-iso | 1 | Q1 | |
| 950. | NO₂ | H | | 1 | Q1 | |

TABLE 3-continued

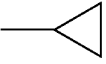

| Compound No. | X | Y | R² | n | Q | Property (n₂₀^D or mp. °C.) |
|---|---|---|---|---|---|---|
| 951. | NO₂ | H | cyclopropyl | 1 | Q6 | |
| 952. | NO₂ | H | cyclopropyl | 1 | Q8 | |
| 953. | NO₂ | H | cyclohexyl | 1 | Q1 | |
| 954. | NO₂ | H | cyclohexyl | 1 | Q6 | |
| 955. | NO₂ | H | phenyl | 1 | Q1 | |
| 956. | NO₂ | H | 2-Cl-phenyl | 1 | Q1 | |
| 957. | NO₂ | H | CHF₂ | 0 | Q1 | |
| 958. | NO₂ | H | CHF₂ | 0 | Q6 | |
| 959. | NO₂ | H | CH₂CH₂CH₂F | 0 | Q1 | |
| 960. | NO₂ | H | CH₂CF₃ | 1 | Q1 | |
| 961. | NO₂ | H | CH₂CF₂CF₃ | 1 | Q1 | |
| 962. | CN | H | CH₃ | 0 | Q1 | |
| 963. | CN | H | CH₃ | 0 | Q2 | |
| 964. | CN | H | CH₃ | 0 | Q4 | |
| 965. | CN | H | CH₃ | 0 | Q5 | |
| 966. | CN | H | CH₃ | 0 | Q6 | |
| 967. | CN | H | CH₃ | 0 | Q7 | |
| 968. | CN | H | CH₃ | 0 | Q8 | |
| 969. | CN | H | CH₃ | 1 | Q1 | |
| 970. | CN | H | CH₃ | 1 | Q3 | |
| 971. | CN | H | CH₃ | 1 | Q4 | |
| 972. | CN | H | CH₃ | 1 | Q6 | |
| 973. | CN | H | CH₃ | 1 | Q8 | |
| 974. | CN | H | C₂H₅ | 0 | Q1 | |
| 975. | CN | H | C₂H₅ | 0 | Q6 | |
| 976. | CN | H | C₂H₅ | 0 | Q7 | |
| 977. | CN | H | C₂H₅ | 1 | Q1 | |
| 978. | CN | H | C₂H₅ | 1 | Q6 | |
| 979. | CN | H | C₂H₅ | 1 | Q7 | |
| 980. | CN | H | C₃H₇-n | 0 | Q1 | |
| 981. | CN | H | C₃H₇-n | 0 | Q6 | |
| 982. | CN | H | C₃H₇-n | 0 | Q7 | |
| 983. | CN | H | C₃H₇-n | 1 | Q1 | |
| 984. | CN | H | C₃H₇-n | 1 | Q6 | |
| 985. | CN | H | C₃H₇-iso | 0 | Q1 | |
| 986. | CN | H | C₃H₇-iso | 0 | Q7 | |
| 987. | CN | H | C₃H₇-iso | 1 | Q1 | |
| 988. | CN | H | cyclopropyl | 1 | Q1 | |

TABLE 3-continued

![structure]

| Compound No. | X | Y | R² | n | Q | Property ($n_{20}^D$ or mp. °C.) |
|---|---|---|---|---|---|---|
| 989. | CN | H | cyclopropyl | 1 | Q6 | |
| 990. | CN | H | cyclohexyl | 1 | Q1 | |
| 991. | CN | H | phenyl | 1 | Q1 | |
| 992. | CN | H | $CHF_2$ | 0 | Q1 | |
| 993. | CN | H | $CH_2CH_2CH_2F$ | 0 | Q1 | |
| 994. | Cl | $CO_2CH_3$ | $CH_3$ | 0 | Q1 | |
| 995. | Cl | $CO_2CH_3$ | $CH_3$ | 1 | Q1 | |
| 996. | Cl | $CO_2CH_3$ | $CH_3$ | 1 | Q6 | |
| 997. | Cl | $CO_2CH_3$ | $CH_3$ | 1 | Q7 | |
| 998. | Cl | $CH_2OCH_3$ | $CH_3$ | 1 | Q1 | |
| 999. | Cl | $CH_2OCH_3$ | $CH_3$ | 1 | Q6 | |
| 1000. | Cl | $CH_2OCH_3$ | $CH_3$ | 1 | Q7 | |
| 1001. | Cl | $CH_2SCH_3$ | $CH_3$ | 1 | Q1 | |
| 1002. | Cl | $CH_2SCH_3$ | $CH_3$ | 1 | Q6 | |
| 1003. | Cl | $CH_2SCH_3$ | $CH_3$ | 1 | Q7 | |
| 1004. | $SCH_3$ | $CO_2CH_3$ | $CH_3$ | 1 | Q1 | |
| 1005. | $SCH_3$ | $CO_2CH_3$ | $CH_3$ | 1 | Q6 | |
| 1006. | $SCH_3$ | $CH_2OCH_3$ | $CH_3$ | 1 | Q1 | |
| 1007. | $SCH_3$ | $CH_2OCH_3$ | $CH_3$ | 1 | Q6 | |
| 1008. | $SCH_3$ | $CH_2SCH_3$ | $CH_3$ | 1 | Q1 | |
| 1009. | $SCH_3$ | $CH_2SCH_3$ | $CH_3$ | 1 | Q6 | |
| 1010. | $SO_2CH_3$ | $CO_2CH_3$ | $CH_3$ | 0 | Q1 | |
| 1011. | $SO_2CH_3$ | $CO_2CH_3$ | $CH_3$ | 1 | Q1 | |
| 1012. | $SO_2CH_3$ | $CO_2CH_3$ | $CH_3$ | 1 | Q6 | |
| 1013. | $SO_2CH_3$ | $CO_2CH_3$ | $CH_3$ | 1 | Q7 | |
| 1014. | $SO_2CH_3$ | $CH_2OCH_3$ | $CH_3$ | 1 | Q1 | |
| 1015. | $SO_2CH_3$ | $CH_2OCH_3$ | $CH_3$ | 1 | Q6 | |
| 1016. | $SO_2CH_3$ | $CH_2OCH_3$ | $CH_3$ | 1 | Q7 | |
| 1017. | $SO_2CH_3$ | $CH_2SCH_3$ | $CH_3$ | 1 | Q1 | |
| 1018. | $SO_2CH_3$ | $CH_2SCH_3$ | $CH_3$ | 1 | Q6 | |
| 1019. | $SO_2CH_3$ | $CH_2SCH_3$ | $CH_3$ | 1 | Q7 | |
| 1020. | $C_2H_5$ | H | $CH_3$ | 0 | Q1 | |
| 1021. | $C_2H_5$ | H | $CH_3$ | 0 | Q6 | |
| 1022. | $OC_2H_5$ | H | $CH_3$ | 1 | Q1 | |
| 1023. | $OC_2H_5$ | H | $CH_3$ | 1 | Q6 | |

SYNTHESIS EXAMPLE 5

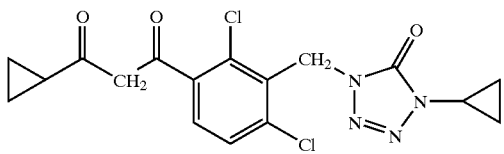

Magnesium (0.18 g) and t-butyl 3-cyclopropyl-3-oxopropionate (1.36 g) were suspended in methanol (16 ml). Then carbon tetrachloride (0.6 ml) was added in small amounts and the mixture stirred for 2 hours. Methanol was distilled off the mixture under reduced pressure and the residue was added with toluene. The toluene was distilled off under reduced pressure to completely eliminate methanol. The residue was dissolved in toluene (40 ml), to which 3-[(4-cyclopropyl-4,5-dihydro-5-oxo-1H-tetrazol-1-yl) methyl]-2,4-dichlorobenzoyl chloride (2.57 g) was added. The mixture was stirred at room temperature for 6 hours and left standing for a night. It was acidified by addition of 3N HCl, extracted with ethyl acetate (100 ml) and dried with anhydrous magnesium sulfate.

Then the residue, obtained by distilling off the ethyl acetate, was dissolved in toluene (40 ml), to which 4-toluenesulfonic acid monohydrate (0.24 g) was added and refluxed for 4 hours upon heating. After cooling, it was extracted with ethyl acetate (150 ml), washed with an aqueous solution of sodium hydrogen carbonate and salt water, and dried with anhydrous magnesium sulfate. The residue, obtained by distilling off of ethyl acetate, was purified by silica column chromatography (ethyl acetate: n-hexane=2:1) to obtain the objective 3-cyclopropyl-1-{3-[(4-cyclopropyl-4,5-dihydro-5-oxo-1H-tetrazol-1-yl) methyl]-2,4-dichlorophenyl}propan-1,3-dione (2.69 g, 70% yield from 3-[(4-cyclopropyl-4,5-dihydro-5-oxo-1H-tetrazol-1-yl)methyl]-2,4-dichlorobenzoic acid). $n_D^{20}$: 1.5972.

SYNTHESIS EXAMPLE 6

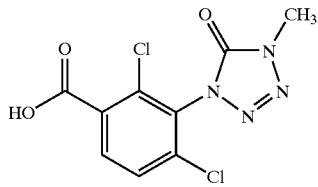

To a solution of methyl 2,4-dichloro-3-(4,5-dihydro-4-methyl-5-oxo-1H-tetrazol-1-yl)benzoate (4.10 g) in dioxane (70 ml), 10N sodium hydroxide (2.0 ml) and water (4ml) were added and the mixture was stirred at 60° C. for 1.5 hours. After concentrating under reduced pressure and the addition of water (50 ml), an aqueous solution of sodium hydroxide was added and washed with ethyl acetate (150 ml). The aqueous layer was acidified with hydrochloric acid and extracted with ethyl acetate. The organic layer was washed with saturated salt water and dried with anhydrous magnesium sulfate. By distilling off of ethyl acetate, the objective 2,4-dichloro-3-(4,5-dihydro-4-methyl-5-oxo-1H-tetrazol-1-yl)benzoic acid (3.42 g, yield 87%) was obtained. mp: 221–225° C.

SYNTHESIS EXAMPLE 7

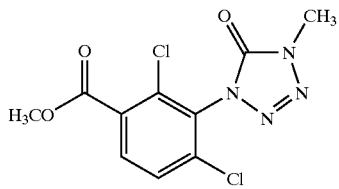

Methyl 2,4-dichloro-3-(4,5-dihydro-5-oxo-1H-tetrazol-1-yl)benzoate (4.00 g), methyl iodide (2.36 g) and potassium carbonate (2.29 g) were suspended in N,N-dimethylformamide (30 ml) and stirred at 60° C. After reaction, cold water was added to the reaction mixture and the mixture was extracted with ethyl acetate (150 ml) and dried with anhydrous magnesium sulfate. By distilling off the ethyl acetate, the objective methyl 2,4-dichloro-3-(4,5-dihydro-4-methyl-5-oxo-1H-tetrazol-1-yl)benzoate (4.13 g, yield 98%) was obtained. mp: 135–137° C.

SYNTHESIS EXAMPLE 8

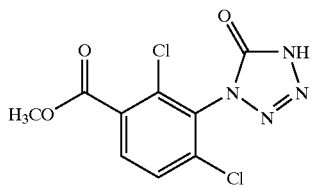

To a solution of trichloromethyl chloroformate (13.41 g) in toluene (150 ml), a toluene solution of methyl 3-amino-2,4-dichlorobenzoate (14.9 g) was added drop by drop under cooling with ice and the solution was refluxed for about 4 hours upon heating. After completion of the reaction the mixture of the residue (obtained by distilling off the toluene from the reaction mixture) and trimethylsilyl azide (11.09 g) was treated with a few drops of boron trifluoride etherate and stirred at 140° C. for 21 hours. After completion of the reaction the excess of trimethylsilyl azide was distilled off and the residue was terated with methanol (10 ml) and stirred. The mixture was added with an aqueous solution of sodium hydroxide and washed with ethyl acetate (500 ml).

The aqueous layer was acidified with hydrochloric acid and extracted with ethyl acetate. The organic layer was washed with saturated salt water and dried with anhydrous magnesium sulfate. By distilling off the ethyl acetate, the objective methyl 2,4-dichloro-3-(4,5-dihydro-5-oxo-1H-tetrazol-1-yl)benzoate (yield 32%) was obtained. mp. 192–193° C.

SYNTHESIS EXAMPLE 9

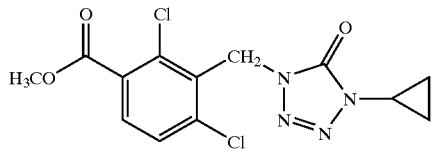

1-Cyclopropyl-5(4H)-tetrazolinone (2.53 g) and potassium carbonate (3.03 g) were suspended in DMF (40 ml), to which methyl 3-bromomethyl-2,4-dichlorobenzoate (5.45 g) in N,N-dimethylformamide (10 ml) was added drop by drop at 5° C. and the mixture was stirred at room temperature for 6 hours. After completion of the reaction the mixture was added with cold water, extracted with ethyl acetate (100 ml) and dried with anhydrous magnesium sulfate. By distilling off the ethyl acetate, the objective methyl 3-[(4-cyclopropyl-4,5-dihydro-5-oxo-1H-tetrazol-1-yl)methyl]-2,4-dichlorobenzoate (5.28 g, yield 84%) was obtained. mp: 99–100° C.

TEST EXAMPLE 1

Test for Herbicidal Effect Against Paddy Field Weeds

Preparation of Formulation of the Active Compound

Carrier: Acetone 5 parts by weight

Emulsifier: Benzyloxypolyglycolether 1 part by weight

A formulation of the active compound is obtained as an emulsion by mixing 1 part by weight of the active compound with the above-mentioned amount of carrier and emulsifier. A prescribed amount of said formulation is diluted with water to prepare a solution for testing.

Test Method

In a greenhouse 3 seedlings of paddy rice (cultivar: Nipponbare) of 2.5 leafstage (15 cm tall) were transplanted in a 500 cm² pot filled with paddy field soil. Then seeds of barnyard grass, smallflower, bulrush, monochoria and broad-leaved weeds (common false pimpernel, Indian toothcup, long stemmed water wort, Ammannia multiflora Roxb., Dopatrium junceum Hammilt etc.) were sown and water was poured on the soil to a depth of about 2–3 cm.

5 days after the rice transplantation a formulation of each active compound prepared according to the aforementioned preparation method was applied to the surface of the water. A water depth of 3 cm was maintained. The herbicidal effect was examined after 3 weeks from the treatment. The herbicidal effect was rated as 100% in the case of complete death and as 0% in the case of no herbicidal effect.

As a result, the compounds of the present invention No. 270, 271 and 288 showed at the chemical amount of 0.25 kg/ha sufficient herbicidal effect against paddy field weeds and showed safety to the transplanted paddy rice.

TEST EXAMPLE 2
Test of Pre-emergence Soil Treatment Against Field Weeds
Test Method
In a greenhouse, on the surface layer of 120 cm² pots filled with soil from the fields, seeds of barnyardgrass, foxtail, common amaranth and knotweed were sown and covered with soil. The prescribed amount of a solution of active ingredients prepared in the same manner as in the above-mentioned Test Example 1 was spread uniformly on the soil surface layer of each test pot. The herbicidal effect was examined on the day after 4 weeks from the treatment.
Results:
The compounds of the present invention No. 84, 271, 282, 321 and 705 showed at the chemical amount of 2.0 kg/ha more than 90% of herbicidal activities against objective weeds (barnyardgrass, foxtail, common amaranth and knotweed).

Test Example 3
Test of Post-Emergence Foliage Treatment Against Field Weeds
Test Method
In a greenhouse, seeds of barnyardgrass, foxtail, common amaranth and knotweed were sown in 120 cm² pots filled with soil from the fields and covered with more soil. 10 days after the sowing and soil coverage (weeds were 2-leafstage in average) the prescribed amount of a solution of the active ingredients prepared in the same manner as in the above-mentioned Test Example I was spread uniformly on the foliage of the test plants in each test pot. The herbicidal effect was examined on the day after 3 weeks from the treatment.
Results:
The compounds of the present invention No. 84, 121, 270, 271, 288, 455, 510, 552 and 705 showed at the chemical amount of 2.0 kg/ha 90% of herbicidal activities against barnyardgrass, foxtail, common amaranth and knotweed.

FORMULATION EXAMPLE 1
(Granule)
To a mixture of 5 parts by weight of compound No. 271, 10 parts by weight of bentonite (montmorillonite), 58 parts by weight of talc and 2 parts by weight of ligninsulphonate, 25 parts by weight of water were added. The mixture is well kneaded, made into granules of 10–40-mesh by extrusion granulation and dried at 40–50° C. to obtain granules.

FORMULATION EXAMPLE 2
(Granule)
95 parts by weight of clay mineral particles having a particle size distribution of 0.2–2 mm are put in a rotary mixer. While rotating it, 5 parts by weight of the compound No. 705 are sprayed together with a liquid diluent into the mixer, wetted uniformly and dried at 40–50° C. to obtain granules.

FORMULATION EXAMPLE 3
(Emulsifiable Concentrate)
30 parts by weight of the compound No. 282, 5 parts by weight of xylene, 8 parts by weight of polyoxyethylenealkyl phenyl ether and 7 parts by weight of calcium alkylbenzenesulphonate are mixed and stirred to obtain an emulsion.

FORMULATION EXAMPLE 4
(Wettable Powder)
15 parts by weight of the compound No. 84, 80 parts by weight of a mixture of white carbon (hydrous amorphous silicon oxide fine particles) and powder clay (1:5), 2 parts by weight of sodium alkylbenzenesulphonate and 3 parts by weight of sodium alkylnaphthalenesulphonate-formalin-polymer are mixed in powder form and made into a wettable powder.

FORMULATION EXAMPLE 5
(Water Dispersible Granule)
20 parts by weight of the compound no. 270, 30 parts by weight of sodium ligninsulphonate, 15 parts by weight of bentonite and 35 parts by weight of calcined diatomaceous earth powder are well mixed, added with water, then extruded using a 0.3 mm screen and dried to obtain a water dispersible granule.

What is claimed is:

1. A tetrazolinone of the formula (I)

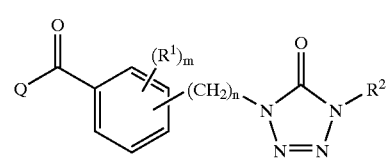

(I)

wherein
R¹ represents halogen, $C_{1-4}$ alkyl, $C_{1-4}$ haloalkyl, $C_{1-4}$ alkoxy, $C_{1-4}$ alkylthio, $C_{1-4}$ alkylsulfonyl, $C_{1-4}$ alkylsulfonyloxy, $C_{2-5}$ alkoxycarbonyl, $C_{2-6}$ alkoxyalkyl, $C_{2-6}$ alkylthioalkyl, nitro, or cyano, R² represents a hydrogen atom; $C_{1-6}$ alkyl; $C_{3-6}$ cycloalkyl that is optionally substituted with halogen or $C_{1-3}$ alkyl; $C_{1-4}$ haloalkyl; or phenyl that is optionally substituted with halogen, $C_{1-3}$ alkyl, $C_{1-3}$ haloalkyl, or nitro, m represents 0, 1, or 2, where when m represents 2, R¹ may be identical or different, n represents 0 or 1, Q represents

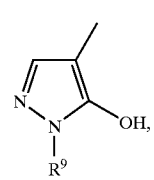

(Q-2)

wherein
R⁹ represents $C_{1-4}$ alkyl.

2. A tetrazolinone of claim 1 wherein
R¹ represents fluoro, chloro, bromo, methyl, ethyl, $C_{1-2}$ haloalkyl, methoxy, ethoxy, methylthio, ethylthio, methylsulfonyl, ethylsulfonyl, methylsulfonyloxy, ethylsulfonyloxy, methoxycarbonyl, ethoxycarbonyl, $C_{2-4}$ alkoxyalkyl, $C_{2-4}$ alkylthioalkyl, nitro, or cyano, R² represents a hydrogen atom; $C_{1-4}$ alkyl; $C_{3-5}$ cycloalkyl that is optionally substituted with fluoro, chloro, bromo, or $C_{1-3}$ alkyl; $C_{1-3}$ haloalkyl; or phenyl that is optionally substituted with fluoro, chloro, bromo, methyl, ethyl, difluoromethyl, or trifluoromethyl, m represents 0, 1, or 2, where when m represents 2, $R^1$ may be identical or different,
n represents 0 or 1,
Q represents

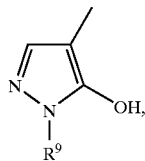

(Q-2)

wherein
   $R^9$ represents $C_{1-3}$ alkyl.
3. A tetrazolinone of claim 1 wherein
   $R^1$ represents chloro, bromo, methyl, trifluoromethyl, methoxy, methylthio, methylsulfonyl, methylsulfonyloxy, methoxycarbonyl, methoxymethyl, methylthiomethyl, or nitro,
   $R^2$ represents a hydrogen atom; methyl, ethyl, n-propyl, isopropyl, or tert-butyl; cyclopropyl that is optionally substituted with fluoro, chloro, methyl, ethyl, or n-propyl; difluoromethyl, 2,2,2-trifluoroethyl, 3-fluoropropyl, or 2,2,3,3,3-pentafluoropropyl; or phenyl that is optionally substituted with fluoro, chloro, methyl, difluoromethyl, or trifluoromethyl,
m represents 0, 1, or 2, where when m represents 2, $R^1$ may be identical or different,
n represents 0 or 1,
Q represents

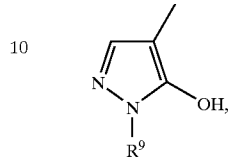

wherein
   $R^9$ represents methyl or ethyl.
4. An herbicidal composition comprising one or more tetrazolinones of claim 1 mixed with extenders and optionally with surface-active agents.
5. A process for combating a weed comprising applying a herbicidally effective amount of a tetrazolinone of claim 1 to the weed and its habitat.

* * * * *